United States Patent
Sharif

(10) Patent No.: US 7,807,629 B1
(45) Date of Patent: Oct. 5, 2010

(54) USE OF BRADYKININ AND RELATED $B_2R$ AGONISTS TO TREAT OCULAR HYPERTENSION AND GLAUCOMA

(75) Inventor: Najam A. Sharif, Arlington, TX (US)

(73) Assignee: Alcon Research, Ltd., Fort Worth, TX (US)

(*) Notice: Subject to any disclaimer, the term of this patent is extended or adjusted under 35 U.S.C. 154(b) by 13 days.

(21) Appl. No.: 12/134,020

(22) Filed: Jun. 5, 2008

Related U.S. Application Data

(60) Provisional application No. 60/942,126, filed on Jun. 5, 2007.

(51) Int. Cl.
*A61K 38/04* (2006.01)
*A61K 38/08* (2006.01)
*C07K 4/00* (2006.01)
*C07K 4/12* (2006.01)

(52) U.S. Cl. .................. 514/2; 514/15; 530/300; 530/314; 530/327; 530/328

(58) Field of Classification Search .............. None
See application file for complete search history.

(56) References Cited

U.S. PATENT DOCUMENTS

| | | | |
|---|---|---|---|
| 5,750,646 A | 5/1998 | Coy et al. | |
| 6,015,818 A | 1/2000 | Oku et al. | |
| 6,127,389 A | 10/2000 | Oku et al. | |
| 6,288,036 B1 | 9/2001 | Kyle et al. | |
| 6,316,413 B1 | 11/2001 | Dodey et al. | |
| 6,358,949 B1 | 3/2002 | DeSimone et al. | |
| 6,420,365 B1 | 7/2002 | Peterson et al. | |
| 6,500,831 B1 | 12/2002 | Sharif | |
| 6,509,366 B2 | 1/2003 | Rachwal et al. | |
| 6,958,349 B2 | 10/2005 | Carson et al. | |
| 2005/0244461 A1* | 11/2005 | Nivaggioli et al. | 424/427 |

FOREIGN PATENT DOCUMENTS

WO   WO/2003/092584 A2   11/2003

OTHER PUBLICATIONS

Bhoola et al., "Bioregulation of kinins: kallikreins, kininogens, and kininases", Pharmacol. Rev. vol. 44, 1080, 1992.
Boels and Schaller, "Identification and characterization of GPR100 as a novel human G-protein-coupled bradykinin receptor", Br. J. Pharmacol. vol. 140 pp. 932-938, 2003.
Chiang et al., "Effects of intravenous infusions of histamine 5-hydroxytryptamine, bradykinin and prostaglandins on intraocular pressure" Arch. Int. Pharmacodyn. Ther. vol. 207 pp. 131-138, 1974.
Cole and Ungar, "Action of bradykinin on intraocular pressure pupillary diameter", Ophthalmic Res. vol. 6 pp. 308-314, 1974.

(Continued)

*Primary Examiner*—Elizabeth C. Kemmerer
(74) *Attorney, Agent, or Firm*—Jason J. Derry

(57) ABSTRACT

The invention provides methods for treating and/or preventing ocular disorders associated with increased intraocular pressure comprising administering a bradykinin $B_2$ receptor agonist to a patient in need thereof.

8 Claims, 5 Drawing Sheets

OTHER PUBLICATIONS

Amblard, et al.; "Design and Synthesis of Potent Bradykinin Agonists Containing a Benzothiazepine Moiety"; J. MEd. Chem.; vol. 42; pp. 4185-4192; 1999.

Funk et al., "Intraocular pressure and systemic blood pressure after administration of vasoactive substances in hypertensive and normal rats" Graefes Arch. Clin. Exp. Ophthalmol. vol. 223 pp. 145-149, 1985.

Gibbs et al., "Neuropeptide Y modulates effects of bradykinin and prostaglandin E2 on trigeinal nociceptors via activation of the Y1 and Y2 receptors", Br. J. Pharmacol. vol. 150, pp. 72-79, 2007.

Greco et al., "Angiotensin-(1-7) potentiates responses to bradykinin but does not change responses to angiotensin I" Can. J. Physiol. Pharmacol., vol. 84, pp. 1163-1175, 2006.

Green and Elijah, "Drug effects on aqueous humor formation and pseudofacility in normal rabbit eyes" Exp. Eye Res. vol. 33, pp. 239-245, 1981.

Drube & Liebmann; "In various tumour cell lines the peptide bradykinin B2 receptor antagonist, Hoe 140 (Icatibant), may act as mitogenic agonist"; British Journal of Pharmacology; vol. 131; pp. 1553-1560; 2000.

Heitsch, "The therapeutic potential of bradykinin B2 receptor agonists in the treatment of cardiovascular disease", Expert Opinion, Invest. Drugs, vol. 12 pp. 759-770, 2003.

Huang et al., "Modulation by bradykinin of angiotensin type 1 receptor-evoked RhoA activation of connective tissue growth factor expression in human lung fibroblasts", Am. J. Physiol. Lung Cell Mol. Physiol. vol. 290 pp. L1291-L1299, 2006.

Ito et al. "Bradykinin inhibits development of myocardial infarction through B2 receptor signalling by increment of regional blood flow around the ischaemic lesions in rats", Br. J. Pharmacol. vol. 138, pp. 225-233, 2003.

Kaufman et al. "Effect of serotonin, histamine and bradykinin on outflow facility following ciliary muscle retrodisplacement in the cynomolgus monkey", Exp. Eye Res. vol. 35 pp. 191-199, 1982.

Feletou, et al.; "Agonistic and antagonistic properties of the bradykinin B2 receptor antagonist, HOE 140, in isolated blood vessels from different species"; British Journal Pharmacology; vol. 112; pp. 683-689; 1994.

Lai et al. "Bombinakinin M gene associated peptide, a novel bioactive peptide from skin secretions of the toad Bombina maxima", Peptides, vol. 24 pp. 199-204, 2003.

Lai et al., "A novel bradykinin-related peptide from skin secretions of toad Bombina maxima and its precursor containing six identical copies of the final product", Biochem. Biophys. Res. Comm. vol. 286 pp. 259, 2001.

Lai et al., "Dynorphin A activates bradykinin receptors to maintain neuropathic pain", Nature Neurosci. vol. 9 pp. 1534-1540 2006.

Lee et al., "Cloning of bradykinin precursor cDNAs from skin of Bombina maxima reveals novel bombinakinin M antagonists and a bradykinin potential peptide", Regul. Peptides, vol. 127 pp. 207, 2005.

Llobet et al., "Bradykinin decreases outflow facility in perfused anterior segments and induces shape changes in passaged BTM cells in vitro", Invest. Ophthalmol. Vis. Res., vol. 40 pp. 113-125, 1999.

Ma et al., "Expression and cellular localization of the kallikrein-kinin system in human ocular tissues", Exp. Eye Res. vol. 63 pp. 19-26, 1996.

Heitsch; "Non-peptide antagonist and agonists of the Bradykinin B2 receptor"; Current Medicinal Chemistry; vol. 9; pp. 913-928; 2002.

Majima et al., "A nonpeptide mimic of bradykinin blunts the development of hypertension in young spontaneously hypertensive rats", Hypertension vol. 35 pp. 437-442, 2000.

Noda et al., "Neuroprotective role of bradykinin because of the attenuation of pro-inflammatory cytokine release from activated microglia", J. Neurochem. vol. 101, pp. 397-410 2007.

O'Rouke et al., "The smooth muscle pharmacology of maximakinin, a receptor-selective, bradykinin-related nonadecapeptide from the venom of the Chinese toad, Bombina maxima", Regul. Peptides vol. 121 pp. 65, 2004.

Regoli, D. and Barabe, "Pharmacology of bradykinin and related kinins", J. Pharmacol. Rev., vol. 32, No. 1, pp. 1-46, 1980.

Schroder et al. "Cloning and functional characterizatioan of the ornithokinin receptor" J. Biol. Chem. vol. 272 pp. 12475-12481, 1997.

Sharif et al. "Human trabecular meshwork cells express functional serotonin-2A (5HT2A) receptors: role in IOP reduction", Invest. Ophthalmol. Vis. Res. vol. 47 pp. 4001-4010, 2006.

Howl & Payne; "Bradykinin receptors as a therapeutic target"; Expert Opinion Ther. Targets; vol. 7; No. 2; pp. 277-285; 2003.

Tamaki et al., "Effect of topical betaxolol on tissue circulation in the human optic nerve head" J. Ocular Pharmacol. Ther. vol. 15 pp. 313-321, 1999.

Marie, et al.; "Constitutive activation of the human bradykinin B2 receptor induced by mutations in transmembrane helices III and VI"; Molecular Pharmacology; vol. 1; pp. 92-101; 1999.

Waki et al., "Reduction of intraocular pressure by topical administration of an inhibitor of the rho-associated protein kinase" Curr. Eye Res. vol. 22 pp. 470-474, 2001.

Tarasevicience-Stewart; Treatment of severe pulmonary hypertension: a bradykinin receptor 2 agonist B9972 causes reduction of pulmonary artery pressure and right ventricular hypertrophy; Peptides; vol. 26; pp. 1292-1300; 2005.

Yokahama et al., "Implication of polymodal receptor activities in intraocular pressure elevation by neurogenic inflammation" Jpn. J. Ophthalomol. vol. 34 pp. 245-255, 1990.

Langlois, et al.; "Development of agonists of endothelin-1 exhibition selectivity towards ETa receptors"; British Journal of Pharmacology; vol. 139; pp. 616-622; 2003.

* cited by examiner

USE OF BRADYKININ AND RELATED $B_2R$ AGONISTS TO TREAT OCULAR HYPERTENSION AND GLAUCOMA

CROSS-REFERENCE TO RELATED APPLICATION

This application claims priority under 35 U.S.C. §119 to U.S. Provisional Patent Application No. 60/942,126 filed Jun. 5, 2007, the entire contents of which are incorporated herein by reference.

FIELD OF THE INVENTION

The invention relates to methods and compositions to treat ocular disorders associated with elevated intraocular pressure (IOP), including, but not limited to, ocular hypertension and glaucoma.

BACKGROUND OF THE INVENTION

Bradykinin (BK) is an endogenous nonapeptide (H-Arg-Pro-Pro-Gly-Phe-Ser-Pro-Phe-Arg-OH; SEQ ID NO: 1) that is generated by cleavage of the precursor polypeptide (kininogen) by specific proteases (kallikriens) within numerous tissues of the body (Regoli, D. and Barabe, J. *Pharmacol. Rev.*, 32, 1-46, 1980; Hall, J. M., *Pharmacol. Ther.*, 56, 131-190, 1992; Leeb-Lundberg et al., *Pharmacol. Rev.* 57: 27-77, 2005). Certain enzymes of the kininase family degrade BK and related peptides and thus inactivate these peptides. All components of the kallkrien/kinin system, including specific receptors activated by BK and related peptides, are present in the human eye cells and tissues (Ma et al., *Exp. Eye Res.* 63: 19-26, 1996; Sharif and Xu, *Exp. Eye Res.* 63: 631-637, 1996).

BK and another endogenous peptide (Lys-BK; Lys-Arg-Pro-Pro-Gly-Phe-Ser-Pro-Phe-Arg; SEQ ID NO: 2) interact with two major BK receptor-subtypes, namely $B_1$ and $B_2$ to produce their biological effects (Regoli, D. and Barabe, J. *Pharmacol. Rev.*, 32, 1-46, 1980; Hall, J. M., *Pharmacol. Ther.*, 56, 131-190, 1992; Leeb-Lundberg et al., *Pharmacol. Rev.* 57: 27-77, 2005). The $B_2$-subtype is found under normal physiological conditions, while the $B_1$-subtype is typically induced during injury or trauma (Hall, J. M., *Pharmacol. Ther.*, 56, 131-190, 1992; Leeb-Lundberg et al., *Pharmacol. Rev.* 57: 27-77, 2005). While the $B_1$-subtype has a low affinity for BK and a high affinity for Des-Arg$^9$-BK (Arg-Pro-Pro-Gly-Phe-Ser-Pro-Phe; SEQ ID NO: 3) and Lys-BK, the $B_2$-subtype has a high affinity for BK and Lys-BK but a low affinity for Des-Arg$^9$-BK. Both receptor subtypes have been cloned and shown to be coupled to G-proteins and phospholipase C and their activation results in the generation of the second messengers inositol trisphosphate ($IP_3$) and diacylglycerol (DAG) (Bhoola et al., *Pharmacol. Rev.* 44: 1080, 1992; Hall, J. M., *Pharmacol. Ther.*, 56, 131-190, 1992; Leeb-Lundberg et al., *Pharmacol. Rev.* 57: 27-77, 2005). While $IP_3$ mobilizes intracellular $Ca^{2+}$ ($[Ca^{2+}]_i$), DAG phosphorylates protein kinase C, and together these events lead to the final biological response such as cell shape change, tissue contraction or fluid secretion or all of the above. Additional events ensuing from elevation of $[Ca^{2+}]_i$ include activation of nitric oxide synthase (NOS) to produce nitric oxide (NO) that in turn activates guanylate cyclase to produce cGMP, and activation of cycloxygenases and/or phospholipase $A_2$ that produce endogenous prostaglandins (PGs) that in turn elevate intracellular cAMP (Leeb-Lundberg et al., *Pharmacol. Rev.* 57: 27-77, 2005; Crider and Sharif, *J. Ocular Pharmacol. Ther.* 17: 59-67, 2001).

Activation of the $B_2$-receptor can also lead to inhibition of cAMP production in host cells transfected with the human recombinant $B_2$ receptors (Meini et al., *Brit. J. Pharmacol.* 143: 938-941, 2004). The majority of the physiological and pathological effects of BK are mediated by the $B_2$-receptor-subtype. However, pharmacological evidence has pointed to two additional BK-receptor subtypes, namely $B_3$ and $B_4$ (Hall, J. M., *Pharmacol. Ther.*, 56, 131-190, 1992; Sharma, *Gen. Pharmacol.*, 24, 267-274, 1993). $B_3$ and $B_4$ receptor subtypes are actually stimulated by certain peptide BK antagonists whereas the $B_1$ and $B_2$ subtypes are blocked by the latter antagonists (Sharma, J. N., *Gen. Pharmacol.*, 24, 267-274, 1993). While the presence of $B_3$ or $B_4$ receptor subtypes in the eye has not been investigated to date, there is precedence for their existence in this organ since there is a robust BK-precursor and BK-generating enzyme pool in human ocular tissues and the presence of $B_1$ and $B_2$ receptors (Ma et al., *Exp. Eye Res.*, 63: 19-26, 1996).

Two new families of peptides related to BK, namely ovikinins (Schroder et al. *J. Biol. Chem.* 272: 12475-12481, 1997) and bombinakinins (Lai et al, *Biochem. Biophys. Res Comm.* 286: 259, 2001; Lai et al., *Peptides*, 24: 199, 2003; O'Rouke et al., *Regul. Peptides* 121: 65, 2004; Lee et al., *Regul. Peptides*, 127: 207, 2005), have been discovered recently that may interact with BK receptors or similar receptors, and which may be useful for lowering IOP. Additionally, a new receptor termed GPR100 has been recently discovered with which BK also interacts (Boels and Schaller, *Br. J. Pharmacol.* 140: 932-938, 2003). Likewise, other selective peptides of the dynorphin family (Lai et al. *Nature Neurosci.* 9: 1534-1540, 2006), neurotensin (Park and Kim, *Cell. Signal.*, 15: 519-527, 2003) and neuropeptide Y (Gibbs et al., *Br. J. Pharmacol.* 150: 72-79, 2007), can activate BK receptors.

Additional useful properties imparted by BK or BK mimetics include the lowering of mRNA of connective tissue growth factor (CTGF) (Huang et al. *Am. J. Physiol. Lung Cell Mol. Physiol.* 290: L1291-L1299, 2006), a fibrotic cytokine that has been implicated in the possible etiology of ocular hypertension by promoting deposition of collagen and fibronectin in the TM area (International Patent Application No. PCT/US2003/012521 to Fleenor et al. published Nov. 13, 2003 as WO 03/092584 and assigned to Alcon, Inc.); BK-induced inactivation of RhoA (*Am. J. Physiol. Lung Cell Mol. Physiol.* 290: L129-L1299, 2006) since Rho kinase inhibitors lower ocular hypertension (Waki et al., *Curr. Eye Res.* 22: 470-474, 2001); BK-induced blunting of systemic hypertension (Majima et al., *Hypertension* 35: 437-442, 2000) and BK-induced increase in blood flow (Ito et al. *Br. J. Pharmacol.* 138: 225-233, 2003) that is beneficial for retinoprotection (Tamaki et al., *J. Ocular Pharmacol. Ther.* 15: 313-321, 1999). In addition, BK and its analogs would be anticipated to be useful therapeutically because BK attenuates the release of pro-inflammatory cytokines from activated microglial cells (Noda et al., *J. Neurochem.* 101: 397-410, 2007).

There are a number of ocular conditions that are caused by, or aggravated by, damage to the optic nerve head, degeneration of ocular tissues, and/or elevated IOP. For example, "glaucomas" are a group of debilitating eye diseases that are a leading cause of irreversible blindness in the United States and other developed nations. Primary Open Angle Glaucoma ("POAG") is the most common form of glaucoma (Quigley, *Br. J. Opthalmol.*, 80: 389-393, 1996). The disease is characterized by the degeneration of the trabecular meshwork, leading to obstruction of the normal ability of aqueous humor to leave the eye without closure of the space (e.g., the "angle") between the iris and cornea (Rohen, *Opthalmol.* 90: 758-765, 1983; (Quigley, *Br. J. Opthalmol.*, 80: 389-393, 1996). A characteristic of such obstruction in this disease is an increased IOP, resulting in progressive visual loss and blindness if not treated appropriately and in a timely fashion. The disease is estimated to affect between 0.4% and 3.3% of all adults over 40 years old. Moreover, the prevalence of the disease rises with age to over 6% of those 75 years or older. Thus, close to 70 million are afflicted by glaucoma (Quigley, *Br. J. Opthalmol.*, 80: 389-393, 1996).

Glaucoma affects three separate tissues in the eye. The elevated IOP associated with POAG is due to morphological and biochemical changes in the trabecular meshwork (TM), a tissue located at the angle between the cornea and iris, and ciliary muscle (CM) bundles. Most of the nutritive aqueous humor exits the anterior segment of the eye through the TM. The progressive loss of TM cells and the build-up of extracellular debris in the TM of glaucomatous eyes leads to increased resistance to aqueous outflow, thereby raising IOP. Elevated IOP, as well as other factors such as ischemia, cause degenerative changes in the optic nerve head (ONH) leading to progressive "cupping" of the ONH and loss of retinal ganglion cells and axons. The detailed molecular mechanisms responsible for glaucomatous damage to the TM, ONH, and the retinal ganglion cells are unknown.

Twenty years ago, the interplay of ocular hypertension, ischemia and mechanical distortion of the optic nerve head were heavily debated as the major factors causing progression of visual field loss in glaucoma. Since then, other factors including excitotoxicity, nitric oxide, absence of vital neurotrophic factors, abnormal glial/neuronal interplay and genetics have been implicated in the degenerative disease process. The consideration of molecular genetics deserves some discussion insofar as it may ultimately define the mechanism of cell death, and provide for discrimination of the various forms of glaucoma. Within the past 10 years, over 15 different glaucoma genes have been mapped and 7 glaucoma genes identified. However, despite such progress, the glaucomas still remain poorly understood.

Glaucoma is a progressive disease which leads to optic nerve damage and, ultimately, total loss of vision. Since there is a good correlation between IOP control and prevention/ reduction of glaucomatous damage in POAG patients (Mao et al., *Am. J. Opthalmol.* 111: 51-55, 1991), several therapeutic agents have been developed to treat ocular hypertension (Clark and Yorio, *Nature Rev. Drug Discovery,* 2: 448-459, 2003; Sharif and Klimko, Ophthalmic Agents, in *Comprehensive Medicinal Chemistry II.*, Vol. 6, Chapter 6.12, p. 297-320; Eds: D. J. Triggle and J. B. Taylor, Elsevier Oxford, 2007). Thus, it is known that elevated IOP can be at least partially controlled by administering drugs which either reduce the production of aqueous humor within the eye, such as beta-blockers and carbonic anhydrase inhibitors, or increase the outflow of aqueous humor from the eye, such as miotics and sympathomimetics. Unfortunately, many of the drugs conventionally used to treat ocular hypertension have a variety of problems. For instance, miotics such as pilocarpine can cause blurring of vision and other visual side effects, which may lead either to decreased patient compliance or to termination of therapy. Systemically administered carbonic anhydrase inhibitors can also cause serious side effects such as nausea, dyspepsia, fatigue, and metabolic acidosis, which side effects can affect patient compliance and/or necessitate the termination of treatment. Another type of drug, beta-blockers, have increasingly become associated with serious pulmonary side effects attributable to their effects on beta-2 receptors in pulmonary tissue. Sympathomimetics, on the other hand, may cause tachycardia, arrhythmia and hypertension. Recently, certain prostaglandins and prostaglandin derivatives have been described in the art as being useful in reducing IOP. Typically, however, prostaglandin therapy for the treatment of elevated IOP is attended by undesirable side-effects, such as irritation and hyperemia of varying severity and duration. There is therefore a continuing need for therapies that control elevated IOP associated with glaucoma without the degree of undesirable side-effects attendant to most conventional therapies.

SUMMARY OF THE INVENTION

The invention provides methods for treating and/or preventing an ocular condition associated with elevated intraocular pressure (IOP), such as ocular hypertension and glaucoma. In certain aspects, a method of the invention comprises administering to a patient a composition comprising a therapeutically effective amount of a bradykinin (BK) $B_2$ receptor ($B_2R$) agonist, preferably metabolically and/or conformationally stabilized peptide or pseudopeptide with one or more non-peptide bonds, in a pharmaceutically acceptable ophthalmic vehicle.

In certain aspects, $B_2R$ agonists of the invention can be advantageously used alone or in combination with other IOP-lowering agents to increase the potency, efficacy and/or duration of the IOP reduction.

In yet other aspects, embodiments disclosed herein provide a method to activate $B_2R$ using peptidic BK analogs and/or mimetics alone or in conjunction with kininase inhibitors in an acceptable carrier(s).

Specific preferred embodiments of the invention will become evident from the following more detailed description of certain preferred embodiments and the claims.

DETAILED DESCRIPTION OF THE INVENTION

Figure 1:
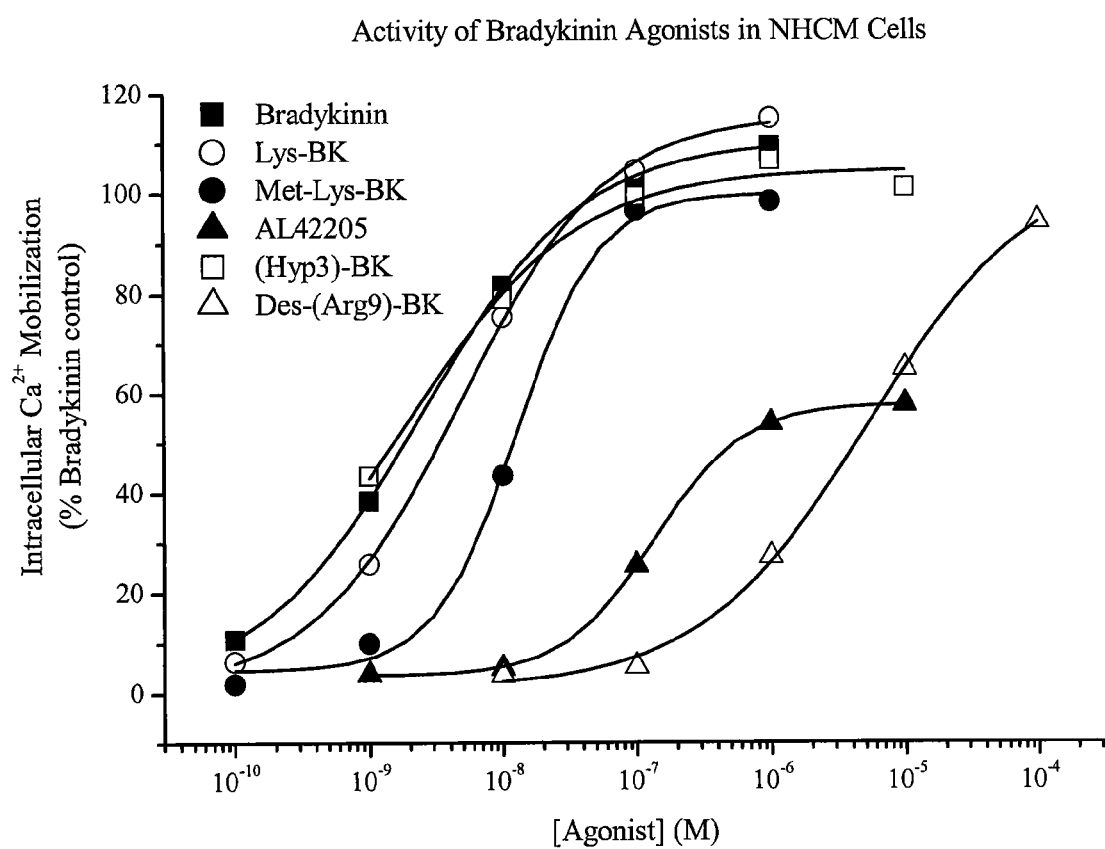
FIG. 1 illustrates the ability of various BK and BK analog agonists to stimulate $[Ca^{2+}]_i$ mobilization in human ciliary muscle (h-CM cells). The maximal BK-induced functional response (set to 100%) was used to calculate the relative stimulation by various concentrations of other agonists.

There are conflicting reports in the literature as to the functions and involvement of bradykinin (BK) in the modulation of intraocular pressure (IOP) in various animal models. Thus, while intravenous infusion of BK apparently lowered IOP (Chiang et al., *Arch. Int. Pharmacodyn. Ther.* 207: 131-138, 1974; Funk et al., *Graefes Arch. Clin. Exp. Opthalmol.* 223: 145-149, 1985), injection of BK directly into the anterior chamber of the eye raised IOP and caused intense miosis (Cole and Ungar, *Ophthalmic Res.* 6: 308-314, 1974; Yokahama et al., *Jpn. J. Ophthalomol.* 34: 245-255, 1990) and increased both aqueous humor inflow and outflow (Green and Elijah, *Exp. Eye Res.* 33: 239-245, 1981). Furthermore, BK either had no effect on aqueous humor outflow (no ciliary muscle retrodisplacement) or decreased outflow (with ciliary muscle retrodisplacement) in cynomolgus monkey eyes upon injection of BK into the eye anterior chamber (Kaufman et al. *Exp. Eye Res.* 35: 191-199, 1982). Additionally, in perfused human and bovine anterior eye segments BK decreased outflow facility (Llobet et al., *Invest. Opthalmol. Vis. Res.*, 40: 113-125, 1999), while another group has recently demonstrated apparent increase in outflow in bovine eyes (Webb et al., *J. Ocular Pharmacol. Ther.* 22: 310-316, 2006). Such conflicting data coupled with an existing patent (U.S. Pat. No. 6,500,831) that contemplated the need for BK antagonists to elicit ocular hypotension has resulted in confusion about the potential role of endogenous BK and related peptides and their receptors in the modulation of IOP and ocular hypertension. Some obvious drawbacks and reasons for the lack of consistent observations noted above are probably related to species differences in the effects of BK on IOP changes, and perhaps due to the different routes of administration of the compound, and on the fact that BK is a peptide that can be inactivated by proteases when it comes into contact with body fluids (Hall, J. M., *Pharmacol. Ther.*, 56, 131-190, 1992).

The invention provides methods for treating or preventing ocular hypertension and ocular diseases associated with elevated intraocular pressure (IOP), such as glaucoma. In certain embodiments, the methods of the invention comprise the step of administering a pharmaceutical composition to the eye of a patient, wherein the composition comprises a therapeutically effective amount of a $B_2R$ agonist, preferably a metabolically and/or conformationally stabilized peptide or a pseudopeptide with one or more non-peptide bonds, and a pharmaceutically acceptable opthalmologic carrier.

In particular embodiments, the invention provides pharmaceutical compositions comprising at least one metabolically and/or conformationally stabilized $B_2R$ agonist or a pseudopeptide with one or more non-peptide bonds. The pharmaceutical compositions of the invention can be used to control IOP in a patient, thereby treating or preventing ocular hypertension and diseases associated with elevated IOP, such as glaucoma. As used herein, the phrases "control IOP" and "controlling IOP" refer to the ability of a pharmaceutical composition of the invention to prevent an increase of a patient's IOP and/or to lower a patient's existing IOP. Thus, a pharmaceutical composition of the invention can be used, for example, to prevent ocular hypertension from progressing into an ocular disease associated with elevated IOP, such as glaucoma. Alternatively, a pharmaceutical composition of the invention can be used, for example, to treat a patient who has been diagnosed with glaucoma, thereby reducing the patient's elevated IOP and improving and/or restoring vision to the patient.

As used herein, the term "patient" includes human and animal subjects.

The term "therapeutically effective amount" refers to the amount of a pharmaceutical composition of the invention determined to produce a therapeutic response in a mammal. Such therapeutically effective amounts are readily ascertained by one of ordinary skill in the art and using methods as described herein.

As used herein, the term "pharmaceutically acceptable ophthalmic carrier" refers to those carriers that cause at most, little to no ocular irritation, provide suitable preservation if needed, and deliver one or more $B_2R$ agonists of the present invention in a homogenous dosage.

The compositions of the invention can be administered to an eye of a patient as solutions, suspensions, or emulsions (dispersions) in a suitable ophthalmic carrier. For example, the compositions can be delivered topically to the eye in the form of drops, sprays, or gels. Alternatively, the compositions can be administered by injection (e.g., intravitreal, intraorbital, and/or subconjunctival and/or sub-tenon injection). The compositions can also be administered by means of an implantable device, which can be attached, for example, to a subconjunctival or intravitreal region of the eye.

In preparing compositions for topical administration, the $B_2R$ agonists are generally formulated from about 0.00005 to about 1.0 percent by weight (wt %). The $B_2R$ agonists are preferably formulated between about 0.0003 to about 0.3 wt % and, most preferably, between about 0.0005 and about 0.03 wt %. In general, the compositions will be solutions, having a pH between about 4.5 and about 7.4. While the precise regimen is left to the discretion of the clinician, the resulting solution or solutions are preferably administered by placing one drop of each solution(s) in each eye one to four times a day, or as directed by the clinician.

Other ingredients which may be desirable to use in the ophthalmic preparations of the present invention include preservatives, co-solvents, buffers, viscosity building agents and penetration enhancers. Viscosity building agents, such as hydroxymethyl cellulose, hydroxyethyl cellulose, methylcellulose, polyvinylpyrrolidine, a polymer matrix such as CAPA4101 or the like, may be added to the compositions of the present invention to improve the retention of the compound in the conjunctival sac or surrounding area. In order to prepare sterile ophthalmic ointment formulations, the BK agonist may be combined with a preservative in an appropriate vehicle, such as white petroleum, mineral oil or liquid lanolin. Sterile ophthalmic gel formulations may be prepared by suspending the $B_2R$ agonist in a hydrophilic base prepared from the combination of, for example, carbopol-940, or the like, according to the methods known in the art for other ophthalmic formulations. Other compositions of the resent invention may contain penetration enhancing agents such as cremephor and tween-80, in the event the BK agonists are less penetrating in the eye.

The terms "pharmaceutical composition" and "composition" as used herein refer to a composition comprising a pharmaceutically acceptable opthalmologic carrier, excipient, or diluent and a BK agonist as described herein that is capable of inducing a desired therapeutic effect (e.g. lowering IOP or preventing an increase in IOP) when properly administered to a patient.

As used herein, a "bradykinin $B_2$ receptor agonist" or "$B_2R$ agonist" refers to a compound that selectively activates the $B_2$ receptor, including BK itself (SEQ ID NO: 1). As used herein, the phrase "selectively activates" refers to a compound that preferentially binds to and activates $B_2R$ with a greater affinity and potency, respectively, than its interaction with the other sub-types or isoforms of the BK receptor family. Compounds that prefer $B_2R$, but that may also activate other BK receptor sub-types, as partial or full agonists, and thus that may have multiple BK receptor activities, are contemplated.

In certain embodiments, a $B_2R$ agonist of the invention is a peptide, such as a BK analog or truncated BK peptide, as described herein. In other embodiments, a $B_2R$ agonist is a non-peptide compound, such as a compound described, for example, in U.S. Pat. No. 6,015,818; U.S. Pat. No. 6,127,389; U.S. Pat. No. 6,958,349; U.S. Pat. No. 6,509,366; U.S. Pat. No. 6,420,365; and U.S. Pat. No. 6,358,949; the disclosures of which are hereby incorporated by reference in their entirety. A $B_2R$ agonist also includes peptide mimetics, metabolically and/or conformationally stabilized peptide analogs, derivatives, and pseudo-peptides with one or more non-peptide bonds, especially containing D-amino acids and/or at least one non-peptide bond. BK and related peptides, and other peptides, mimetics and/or metabolically and/or conformationally stabilized peptide analogs and/or derivatives or pseudopeptides with one or more non-peptide bonds, especially containing D-amino acids and/or at least one non-peptide bond, of the invention are useful in lowering intraocular pressure, and thus are useful in the treatment of ocular hypertension or glaucoma.

In one embodiment, the $B_2R$ agonist in a method of the invention is not FR-190997 or Compound A (compound 38 as shown in Sawada et al., *J. Med. Chem.* 47: 2853-2863, 2004), whose chemical structures are shown below.

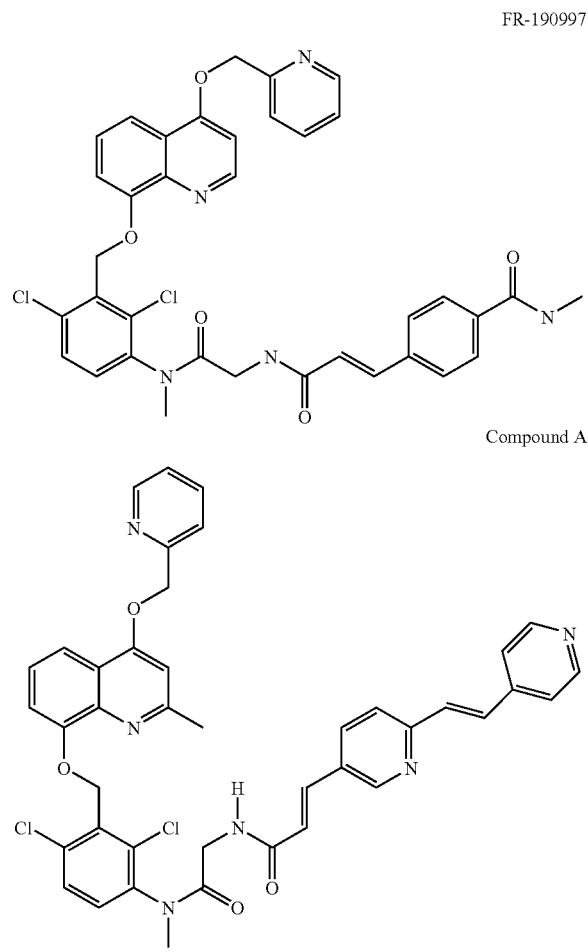

FR-190997

Compound A

"Peptide mimetics" (see, for example, Fauchere, *Adv. Drug Res.* 15: 29, 1986; and Evans et al., *J. Med. Chem.* 30: 1229, 1987), which are incorporated herein by reference for any purpose), can be developed with the aid of computerized molecular modeling. Peptide mimetics that are structurally similar to therapeutically useful BK agonist peptides may be used to produce a similar therapeutic or prophylactic effect. Generally, peptide mimetics are structurally similar to a paradigm polypeptide (i.e., a polypeptide that has a biochemical property or pharmacological activity), but have one or more peptide linkages optionally replaced by a linkage such as: —$CH_2NH$—, —$CH_2S$—, —$CH_2$—$CH_2$—, —CH=CH— (cis and trans), —$COCH_2$—, —$CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used in certain embodiments to generate more stable BK peptide agonists. In addition, conformationally-constrained peptides comprising a consensus sequence or a substantially identical consensus sequence variation may be generated by methods known in the art (Rizo and Gierasch, 1992, *Ann. Rev. Biochem.* 61: 387), incorporated herein by reference for any purpose); for example, by adding internal cysteine residues capable of forming intramolecular disulfide bridges which cyclize the peptide.

Metabolically and/or conformationally stabilized BK analogs useful in practicing the current invention include JMV-1116 (S-isomer; Compound 1) and its R-isomer (Compound 2) (Amblard et al. *J. Med. Chem.* 42: 4185-4192, 1999), Compound 4 (see below; Amblard et al. *J. Med. Chem.* 42: 4185-4192, 1999), RMP-7 (lobradamil; Cereport®; Compound 4 below; Amblard et al. *J. Med. Chem.* 42: 4185-4192, 1999; Heitsch, *Exp. Opin. Invest. Drugs,* 12: 759-770, 2003) and B9972 (Compound 5 below; Taraseviciene-Stewart et al., *Peptides* 26: 1292-1300, 2005). Several examples of $B_2R$ agonists useful in the methods of the invention are listed below.

Lys-Arg-Pro-Pro-Gly-Phe-Ser-Pro-Phe-Arg (SEQ ID NO: 2; Lys-BK);

H-D-Arg-Arg-Pro-Hyp-Gly-Thi-Ser-(D-BT)-Arg-OH (SEQ ID NO: 4; JMV1116, S-isomer; Compound 1);

H-D-Arg-Arg-Pro-Hyp-Gly-Thi-Ser-(D-BT)-Arg-OH (SEQ ID NO: 4; JMV 1116, R-isomer; Compound 2);

H-Arg-Pro-Pro-Gly-Phe-Ser-(D-BT)-Arg-OH (SEQ ID NO: 5; Compound 3);

H-Arg-Pro-Hyp-Gly-Thi-Ser-Pro-4-Me-Tyrψ($CH_2NH$)-Arg-OH (SEQ ID NO: 6; RMP-7; Compound 4; where $CH_2NH$ denotes a reduced peptide bond between the 4-Metyrosine and arginine amino acids);

D-Arg-Arg-Pro-Hyp-Gly-Igl-Ser-Oic-Igl-Arg.TFA (SEQ ID NO: 7; B9972; Compound 5);

H-D-Arg-Arg-Pro-Hyp-Gly-Thi-Ser-D-Tic-Oic-Arg-OH (SEQ ID NO: 8; HOE-140; Icatibant; Compound 6);

Met-Lys-Arg-Pro-Pro-Gly-Phe-Ser-Pro-Phe-Arg (SEQ ID NO: 9; Met-Lys-BK);

Ile-Ser-Arg-Pro-Pro-Gly-Phe-Ser-Pro-Phe-Arg (SEQ ID NO: 10; Ile-Ser-BK); and

Arg-Pro-Hyp-Gly-Phe-Ser-Pro-Phe-Arg ($Hyp^3$-BK; SEQ ID NO: 11).

(D=D configuration of amino acid; (D-BT)=(3S)[amino]-5-(carbonylmethyl)-2,3-dihydro-1,5-benzothiazepin-4(5H)-one; Hyp=trans-4-Hydroxy-L-proline; Igl=α-(2-Indanyl) glycine; Oic=Octahydroindole-2-carboxylic acid; Thi=O-(2-thienyl)-alanine; Tic=L-1,2,3,4-Tetrahydroisoquinoline-3-carbonyl; TFA=trifluoroacetic acid)

Additionally, other agents that activate the $B_2R$ receptor(s) directly or indirectly are contemplated to be useful for the invention. Accordingly, peptides (or non-peptides) of the dynorphin family (Lai et al., *Nature Neurosci.* 9: 1534-1540 2006) and/or ovokinin family (*Peptides,* 16: 785-790, 1999; Schroder et al. *J. Biol. Chem.* 272: 12475-12481, 1997), and bombinakinins (Lai et al, *Biochem. Biophys. Res Comm.* 286: 259, 2001; Lai et al., *Peptides,* 24: 199, 2003; O'Rouke et al., *Regul. Peptides* 121: 65, 2004; Lee et al., *Regul. Peptides,* 127: 207, 2005) that activate $B_2R$ are also useful agents in the methods of the invention. In addition, agonists of GPR100 are also useful in the methods of the invention, as well as other peptide potentiators of BK action, such as angiotensin-(1-7) (Greco et al., *Can. J. Physiol. Pharmacol.* 84: 1163-1175, 2006).

The aforementioned stabilized $B_2R$ agonists may be administered in combination with each other or with one or more of other BK-based peptide agonists, including peptide analogs of BK such as Lys-BK (kallidin) (Lys-Arg-Pro-Pro- Gly-Phe-Ser-Pro-Phe-Arg; SEQ ID NO: 2), Met-Lys-BK (Met-Lys-Arg-Pro-Pro-Gly-Phe-Ser-Pro-Phe-Arg; SEQ ID NO: 9), Ile-Ser-BK (Ile-Ser-Arg-Pro-Pro-Gly-Phe-Ser-Pro-Phe-Arg; SEQ ID NO: 10), and Hyp$^3$-BK (Arg-Pro-Hyp-Gly-Phe-Ser-Pro-Phe-Arg; SEQ ID NO: 11), along with other analogs and fragments of the BK-related peptides (Bhoola et al., *Pharmacol. Rev.* 44: 1080, 1992; Hall, J. M., *Pharmacol. Ther.*, 56, 131-190, 1992; Leeb-Lundberg et al., *Pharmacol. Rev.* 57: 27-77, 2005; Sharif and Xu, *Exp. Eye Res.* 63: 631-637, 1996), available commercially from Bachem Biosciences (King of Prussia, Pa.). Specific BK analogs include: BK itself; p-chloro-Phe$^{5,8}$-BK (SEQ ID NO: 12); 3,4-dehydro-Pro$^{2,3}$-BK (SEQ ID NO: 13); 3,4-dehydro-Pro$^{2,3}$, des-Arg$^9$-BK (SEQ ID NO: 14); Lys-BK-Ser-Val-Gln-Val-Ser (SEQ ID NO: 15); Lys-Ala$^3$-BK (SEQ ID NO: 16); Lys-Des-Arg$^9$-BK (SEQ ID NO: 17); Lys-(Hyp$^3$)-BK (SEQ ID NO: 18); Lys-Tyr-BK (SEQ ID NO: 19); D-Phe$^7$-BK (SEQ ID NO: 20); (Thr$^6$)-BK (SEQ ID NO: 21); Tyr-BK (SEQ ID NO: 22); (Tyr$^8$)-BK (SEQ ID NO: 23); H-Met-Lys-Arg-Ser-Arg-Gly-Pro-Ser-Pro-Arg-Arg-OH (SEQ ID NO: 24; BK-like neuropeptide); and H-Arg-Ser-Arg-Gly-Pro-Ser-Pro-Arg-Arg-OH (SEQ ID NO: 25).

In view of the fact that the classic peptide BK B$_2$-receptor antagonist, Hoe-140 (Icatibant; Compound 6 above), sometimes exhibits agonist activity in certain tissues and cells (Feletou et al., *Br. J. Pharmacol.* 112: 683-689, 1994; Schroder et al. *J. Biol. Chem.* 272: 12475-12481, 1997; Marie et al., *Mol. Pharmacol.* 55: 92-101, 1999; Drube and Liebmann, *Br. J. Pharmacol.* 131: 1553-1560, 2000; Howl and Payne, *Expert Opin. Ther. Targets,* 7: 277-285, 2003). Icatibant is also considered a BK agonist useful in a method of the invention.

Other BK receptor activating peptides of the invention include B$_2$R agonists described in U.S. Pat. Nos. 6,316,413; 6,288,036; 6,015,818; and 5,750,646; all of which are incorporated by reference in their entirety.

In order to reduce possible ocular side-effects such as redness (hyperemia) or irritation, the compositions of this invention can be converted to suitable pro-drugs by incorporation of acceptable functional groups to the peptide B$_2$R agonists such that the prodrug would readily penetrate the cornea and be then hydrolyzed to release the active species of the conjugate molecule. This would reduce the ocular surface exposure to the drug and thus result in reduced ocular surface side-effects. Such a prodrug approach is well known to those skilled in the art (e.g. for ocular hypotensive prostaglandins isopropyl esters or amides are known; Stjernschantz et al. *Adv. Prostaglandin. Thrombox. Leukotr. Res.,* 23: 513-518, 1995; Woodward et al. *J. Pharmacol. Exp. Ther.* 305:772-785, 2003).

In other embodiments, a pharmaceutical composition of the invention comprising a stabilized peptide B$_2$R agonist or a pseudopeptide with one or more non-peptide bonds can be administered to a patient alone or in combination with other IOP-lowering agents to increase the potency, efficacy and/or duration of the IOP reduction. Numerous agents known to lower IOP include have been previously described (Sugrue, *J. Med. Chem.* 40: 2793-2809, 1997; Clark and Pang, *Expert Opin. Emerg. Drugs,* 7: 141-163, 2002; Sharif and Klimko, Ophthalmic Agents, in *Comprehensive Medicinal Chemistry II.*, Vol. 6, Chapter 6.12, p. 297-320; Eds: D. J. Triggle and J. B. Taylor, Elsevier Oxford, 2007) including, but not limited to, carbonic anhydrase inhibitors, beta-blockers, prostaglandins, alpha-2 agonists, serotonin-2 agonists, alpha-1 antagonists, dopamine agonists, Rho kinase inhibitors, myosin-II Ca$^{2+}$-ATPase inhibitors, matrix metalloproteinase activators, Activator protein-1 (AP-1) activators (U.S. Pat. No. 7,005, 446), atrial natriuretic peptide receptor-B agonists (Potter and Hunter, *J. Biol. Chem.* 276: 6057-6060, 2001; Scotland and Ahluwalia, *Pharmacol. Ther.* 105: 85-93, 2005), K$^+$-channel blockers (European patent EP1772514) and maxi-K-channel activators (Park et al. *J. Pharmacol. Sci.,* 92: 218-227, 2003; Stumpff et al., *Exp. Eye Res.* 80: 697-708, 2005), phosphodiesterase inhibitors (Menniti et al. *Nat. Rev. Drug Discov.,* 5: 660-670, 2006), stimulators/activators of membrane-bound and cytosolic soluble adenylyl and/or guanylyl cyclases (Evgenov et al. *Nature Rev. Drug Discovery* 5: 755-768, 2006). Other compounds and compound classes described for lowering IOP are also useful for the current invention (Clark and Yorio, *Nature Rev. Drug Discovery,* 2: 448-459, 2003; and in Sharif and Klimko, Ophthalmic Agents, in *Comprehensive Medicinal Chemistry II.*, Vol. 6, Chapter 6.12, p. 297-320; Eds: D. J. Triggle and J. B. Taylor, Elsevier Oxford, 2007; International Publication No. WO 2006/041875; U.S. Pat. No. 7,005,446). Dual and multipharmacophoric agents can be also contemplated and synthesized by those skilled in the art of conjugating B$_2$R agonists with one or more of the agents mentioned above or cited in the publications above.

Just as nitric oxide (NO) liberated de novo from NO-donors or other biological processess have demonstrated physiological and pathological roles, two other compounds, carbon monoxide (CO; Snyder et al., *Brain Res. Rev.* 26: 167-175, 1998) and hydrogen sulfide (H$_2$S; Boehning and Snyder, *Ann. Rev. Neurosci.* 26: 1050131, 2003; Kimura et al., *Antioxid. Redox Signal.* 7: 795-803, 2005), produced endogenously or delivered exogenously also mediate important biological functions. While CO appears to be able to activate soluble guanylyl cyclase (sGC), and NO can increase CO production (Leffler et al., *Am. J. Physiol. Heart Circ. Physiol.* 289: H1442-H1447, 2005), CO and NO can also act synergistically (Stone and Marletta, Chem. Biol. 5: 255-261, 1998; Sharma and Magde, Methods: 19: 494-505, 1999) Thus, sGC may be activated by NO and CO. Although H$_2$S has not been shown yet to activate sGC, because it relaxes smooth muscle (Kimura et al., *Antioxid. Redox Signal.* 7: 795-803, 2005) it is likely that sGC is involved in this process. Also, H$_2$S has recently been shown to lower IOP in rabbits (PCT Application WO 2006/119258). Therefore, in some embodiments, the bradykinin receptor agonists may be advantageously combined with or conjugated with NO-donors and/or CO-donors (tricarbonylchloro [glycinato] ruthenium, tricarbonylchloro [glutamic acidato] ruthenium, tricarbonylchloro [lysinato] ruthenium; tricarbonylchloro [alanato] ruthenium, (Rodella et al., *Free Radical Biol. Med.* 40: 2198-2205, 2006); tricarbonyldichlororuthenium (II) dimer, (Srisook et al., *Biochem. Pharmacol.* 71: 307-318, 2006)), and/or H$_2$S-donors (NaHS; NaS) to achieve synergistic or additive reduction in IOP.

A pharmaceutical composition of the invention may also include an agent that is a source of NO. NO-donors usually cause hyperemia and typically do not exhibit high efficacy in vivo for IOP-lowering. However, a derivative of the anti-epileptic drug gabapentin, NCX8001 ([1-(aminomethyl-cyclohexane acetic acid 3-(nitroxymethyl)phenyl ester]), has been synthesized and shown to be bioavailable and to be a slow releaser of NO and that activates soluble guanylate cyclase (Wu et al *Br. J. Pharmacol.* 141: 65-74, 2003). The slow NO-releasing compound NCX8001 may readily penetrate the cornea and be hydrolyzed in the aqueous humor to release NO to lower IOP, thereby limiting its hyperemic potential. Therefore, in some embodiments, NCX8001 may be included in a pharmaceutical composition for ocular administration to lower IOP. Other agents that may prove suitable NO donors for lowering IOP include nitroparacetamol and nitroflurbiprofen (*Eur. J. Pharmacol.* 483: 317-322, 2004) and nitroglycerin, isosorbide, sodium nitropruside, minoxidil and molsidomine also lower IOP (Nathanson *Eur. J. Pharmacol.* 147: 155-156, 1988; Nathanson, *J. Pharmacol. Exp. Ther.* 260: 956-965, 1992; U.S. Pat. No. 5,500,230).

A phosphodiesterase inhibitor is a drug that blocks one or more of the subtypes of the enzyme phosphodiesterase (PDE), therefore preventing the inactivation of the intracellular second messengers, cyclic adenosine monophosphate (cAMP) and cyclic guanosine monophosphate (cGMP), by the respective PDE subtype(s). Of these, there are at least two types, non-selective and selective. Since cAMP and cGMP are known to relax ciliary muscle (Stumpff et al. *Exp. Eye Res.* 80: 697-708, 2005; Wiederholt et al. *Prog. Retinal Eye Res.* 19: 271-295, 2000), a process that leads to relaxation of the TM and thus resulting in an increase in the aqueous humor outflow (Stumpff et al. *Exp. Eye Res.* 80: 697-708, 2005; Wiederholt et al. *Prog. Retinal Eye Res.* 19: 271-295, 2000). Thus, PDE inhibitors could be advantageously combined with $B_2R$ agonists to enhance the efficacy and/or duration of IOP-lowering induced the BK agonists. Various examples of non-selective phosphodiesterase inhibitors include (1) caffeine; (2) bronchodilator theophylline; and, (3) IBMX (3-isobutyl-1-methylxanthine), the latter of which, at least, is used as investigative tool in pharmacological research. Of the selective inhibitors, there are various ones typically related to the inhibitors subtype.

Examples of PDE1-selective inhibitors are Vinpocetine and IC224 (Menniti et al., *Nature Rev. Drug Discov.*, 5: 660-670, 2006).

Examples of PDE2-selective inhibitors are erythro-9-(2-hydroxy-3-nonyl)-adenine (EHNA) and BAY 60-7550 (Menniti et al., *Nature Rev. Drug Discov.*, 5: 660-670, 2006).

Examples of a PDE3-selective inhibitors are enoximone, milrinone, and cilostamide. All are used clinically for short-term treatment of cardiac failure. Clinically these drugs mimic sympathetic stimulation and increase cardiac output (Menniti et al., *Nature Rev. Drug Discov.*, 5: 660-670, 2006). Further suitable examples are disclosed in U.S. Pat. No. 6,156,753, the contents of which are hereby incorporated by reference as if it were presented herein in its entirety.

An example of a PDE4-selective inhibitors is rolipram. It is used as investigative tool in pharmacological research. PDE4 is the major cAMP-metabolizing enzyme found in inflammatory and immune cells. PDE4 inhibitors have potential as anti-inflammatory drugs especially in airway diseases. They suppress the release of inflammatory signals, such as, but not limited to, cytokines, and inhibit the production of reactive oxygen species. PDE4 inhibitors have a high therapeutic and commercial potential as non-steroidal disease controllers in inflammatory airway diseases such as asthma, COPD and rhinitis (Menniti et al., *Nature Rev. Drug Discov.*, 5: 660-670, 2006). Further suitable examples are disclosed in U.S. Pat. No. 6,127,363, the contents of which are hereby incorporated by reference as if it were presented herein in its entirety.

Examples of PDE5-selective inhibitors are sildenafil, tadalafil, vardenafil, udenafil, and avanafil. A main use for these PDE5 inhibitors are remedies for erectile dysfunction (Menniti et al., *Nature Rev. Drug Discov.*, 5: 660-670, 2006). Further suitable compounds are those disclosed in PCT Applications WO 94/28902, WO 96/16644, and WO 01/19802, the contents of all which are hereby incorporated by reference as if they were presented herein their entirety, including, but not limited to the griseolic acid derivatives, 2-phenylpurinone derivatives, phenylpyridone derivatives, fused and condensed pyrimidines, pyrimidopyrimidine derivatives, purine compounds, quinazoline compounds, phenylpyrimidinone derivative, imidazoquinoxalinone derivatives, pyrazolopyrimidinones, such as, but not limited to, 5-(2-ethoxy-5-morpholinoacetylphenyl)-1-methyl-3-n-propyl-1,6-dihydro-7H-pyrazolo[4,3 d]pyrimidin-7-one, 5-(5-morpholinoacetyl-2-n-propoxyphenyl)-1-methyl-3-n-propyl-1,6-dihydro-7H-pyrazolo[4,3-d]pyrimidin-7-one, 5-[2-ethoxy-5-(4-methyl-1-piperazinylsulfonyl)-phenyl]-1-methyl-3-n-propyl-1,6-dihydro-7H-pyrazolo[4,3-d]pyrimidin-7-one, 5-[2-allyloxy-5-(4-methyl-1-piperazinylsulfonyl)-phenyl]-1-methyl-3-n-propyl-1,6-dihydro-7H-pyrazolo[4,3-d]pyrimidin-7-one, 5-[2-ethoxy-5-[4-(2-propyl)-1-piperazinylsulfonyl)-phenyl]-1-methyl-3-n-propyl-1,6-dihydro-7H-pyrazolo[4,3-d]pyrimidin-7-one, 5-[2-ethoxy-5-[4-(2-hydroxyethyl)-1-piperazinylsulfonyl)phenyl]-1-methyl-3-n-propyl-1,6-dihydro-7H-pyrazolo[4,3-d]pyrimidin-7-one, 5-[5-[4-(2-hydroxyethyl)-1-piperazinylsulfonyl]-2-n-propoxyphenyl]-1-methyl 1,3-n-propyl-1,6-dihydro-7H-pyrazolo[4,3-d]pyrimidin-7-one, 5-[2-ethoxy-5-(4-methyl-1-piperazinylcarbonyl)phenyl]-1-methyl-3-n-propyl-1,6-dihydro-7H-pyrazolo[4,3-d]pyrimidin-7-one, 5-[2-ethoxy-5-(1-methyl-2-imidazolyl)phenyl]-1-methyl-3-n-propyl-1,6-dihydro-7H-pyrazolo[4,3-d]pyrimidin-7-one, 1,3-dimethyl-5-benzylpyrazolo[4,3-d]pyrimidine-7-one, 2-(2-propoxyphenyl)-6-purinone, 6-(2-propoxyphenyl)-1,2-dihydro-2-oxypyridine-3-carboxamide, 2-(2-propoxyphenyl)-pyrido[2,3-d]pyrimid-4(3H)-one, 7-methylthio-4-oxo-2-(2-propoxyphenyl)-3,4-dihydro-pyrimido[4,5-d]pyrimidine, 6-hydroxy-2-(2-propoxyphenyl) pyrimidine-4-carboxamide, 1-ethyl-3-methylimidazo[1,5a] quinoxalin-4(5H)-one, 4-phenylmethylamino-6-chloro-2-(1-imidazoloyl)quinazoline, 5-ethyl-8-[3-(N-cyclohexyl-N-methylcarbamoyl)-propyloxy]-4,5-dihydro-4-oxo-pyrido[3,2-e]-pyrrolo[1,2-a]pyrazine, 5'-methyl-3'-(phenylmethyl)-spiro[cyclopentane-1,7'(8'H)-(3'H)-imidazo[2,1-b]purin]-4' (5'H)-one, 1-[6-chloro-4-(3,4-methylenedioxybenzyl)-aminoquinazolin-2-yl)piperidine-4-carboxylic acid, (6R, 9S)-2-(4-trifluoromethyl-phenyl)methyl-5-methyl-3,4,5,6a, 7,8,9,9a-octa hydrocyclopent[4,5]-imidazo[2,1-b]-purin-4-one, 1-t-butyl-3-phenylmethyl-6-(4-pyridyl)pyrazolo[3,4-d]-pyrimid-4-one, 1-cyclopentyl-3-methyl-6-(4-pyridyl)-4, 5-dihydro-1H-pyrazolo [3,4-d]pyrimid-4-one, 2-butyl-1-(2-chlorobenzyl)-6-ethoxy-carbonylbenzimidaole, 2-(4-carboxy-piperidino)-1-4-(3,4-methylenedioxy-benzyl) amino-6-nitroquinazoline and 2-phenyl-8-ethoxycycloheptimidazole.

The PDE6's are distributed in the retina and have been implicated with retinal degeneration (Menniti et al., *Nature Rev. Drug Discov.*, 5: 660-670, 2006). Selective inhibitors comprise sildenafil, zaprinast, and dipyridamole.

An example of a PDE7-selective inhibitor is Dipyridamole. The PDE8's are distributed throughout the cortex, striatum, hippocampus, and cerebellum and have been implicated with Parkinson's disease and psychosis (Menniti et al., *Nature Rev. Drug Discov.*, 5: 660-670, 2006).

An example of a PDE8-selective inhibitor is Dipyridamole. The PDE8's are distributed throughout the cortex, striatum, and hippocampus and have been implicated with Alzheimer's disease (Menniti et al., *Nature Rev. Drug Discov.*, 5: 660-670, 2006).

An example of a PDE9-selective inhibitor is BAY 73-6691. The PDE9's are distributed throughout the brain and have been implicated with neurodegeneration and cognitive issue (Menniti et al., *Nature Rev. Drug Discov.*, 5: 660-670, 2006).

Examples of PDE10-selective inhibitors include papaverine and PQ-10. The PDE10's have been implicated with psychosis (Menniti et al., *Nature Rev. Drug Discov.*, 5: 660-670, 2006).

An example of a PDE11-selective inhibitor is tadalafil (Menniti et al., *Nature Rev. Drug Discov.*, 5: 660-670, 2006).

Pharmaceutical compositions of the invention can also be advantageously combined with suitable neuroprotective agents such as memantine, eliprodil, $Ca^{2+}$-channel blockers, betaxolol, Rho kinase inhibitors, etc (Clark and Yorio, *Nature Rev. Drug Discovery*, 2: 448-459, 2003; and in Sharif and Klimko, Ophthalmic Agents, in *Comprehensive Medicinal Chemistry II.*, Vol. 6, Chapter 6.12, p. 297-320; Eds: D. J. Triggle and J. B. Taylor, Elsevier Oxford, 2007) to obtain IOP-lowering and protection of retinal ganglion cells (RGC). Since angiotensin converting enzyme (ACE) inhibitors appear to potentiate the effects of endogenous and exogenous BK independent of blocking BK inactivation, and ACE and $B_2$-receptors form a complex (Chen et al., *FASEB J.* 13: 2261-2270, 2006), a combination of BK agonists and ACE inhibitors (e.g. captopril; omapatrilat; enalapril, etc) may also be useful and superior to BK agonists alone for lowering IOP and RGC protection.

As demonstrated in the Examples below, $B_2R$ agonists can increase outflow of aqueous humor in the eye, thereby lowering intraocular pressure (IOP). In certain embodiments, the invention provides methods for lowering IOP comprising administering to a patient in need thereof a therapeutically effective amount of a peptidic or non-peptidepeptidic $B_2R$ agonist in combination with an aqueous humor inflow inhibitor. In other embodiments, the invention provides pharmaceutical compositions comprising at least one non-peptide or peptide $B_2R$ agonist and/or at least one aqueous humor inflow inhibitor. The combination therapy of the invention provides the benefit of lowering IOP by two mechanisms, including inducing uveoscleral outflow of aqueous humor and inhibiting aqueous humor inflow, which can allow for reduced dosages of the compounds thereby lowering the risk of side effects. In certain embodiments, the $B_2R$ agonist and aqueous humor inflow inhibitor are administered concurrently in separate pharmaceutical compositions. In other embodiments, the $B_2R$ agonist and aqueous humor inflow inhibitor are administered formulated together in a pharmaceutical composition. In yet other embodiments, the $B_2R$ agonist and aqueous humor inflow inhibitor are administered sequentially in separate pharmaceutical compositions.

Non-limiting examples of "aqueous humor inflow inhibitors" include β-blockers (e.g. betaxolol; timolol; levobunolol; U.S. Pat. Nos. 4,883,814 and 6,399,605; Clark and Yorio, *Nature Rev. Drug Discovery*, 2: 448-459, 2003; and in Sharif and Klimko, Ophthalmic Agents, in *Comprehensive Medicinal Chemistry II.*, Vol. 6, Chapter 6.12, p. 297-320; Eds: D. J. Triggle and J. B. Taylor, Elsevier Oxford, 2007), α-2 agonists (e.g. brimonidine; apraclonidine; U.S. Pat. Nos. 5,212,196; 5,612,364; U.S. Pat. Nos. 4,883,814 and 6,399,605; Clark and Yorio, *Nature Rev. Drug Discovery*, 2: 448-459, 2003; and in Sharif and Klimko, Ophthalmic Agents, in *Comprehensive Medicinal Chemistry II.*, Vol. 6, Chapter 6.12, p. 297-320; Eds: D. J. Triggle and J. B. Taylor, Elsevier Oxford, 2007), carbonic anhydrase inhibitors (e.g. brinzolamide; dorzolamide; U.S. Pat. No. 5,153,192; U.S. Pat. No. 5,240,923; U.S. Pat. No. 5,464,831; U.S. Pat. No. 5,538,966; U.S. Pat. No. 5,620,970; U.S. Pat. No. 6,242,441; U.S. Pat. No. 6,242,442; and U.S. Pat. No. 6,316,441); serotonin-2 agonists (e.g. R-DOI; α-methyl-serotonin; U.S. Pat. No. 6,664,286), and other classes of compounds that exert their IOP-lowering effects in whole or in part by inhibiting the production of aqueous humor (inflow pathway) (Clark and Yorio, *Nature Rev. Drug Discovery*, 2: 448-459, 2003; and in Sharif and Klimko, Ophthalmic Agents, in *Comprehensive Medicinal Chemistry II.*, Vol. 6, Chapter 6.12, p. 297-320; Eds: D. J. Triggle and J. B. Taylor, Elsevier Oxford, 2007).

$B_2R$ agonists of the present invention may be readily elucidated by utilizing cell-based and/or tissue-based functional assays and animal models as follows.

Receptor Binding Assay:

Agents that can specifically bind to native or human recombinant BK receptors, preferably $B_2R$, and thus displace radiolabeled BK or its analog or its mimetic from the receptors can be discovered using radioreceptor binding techniques as described by Sharif and Whiting (*Neurochem. Int.* 18: 89-96, 1991) and Wiernas et al. (*Brit. J. Pharmacol.* 123: 1127-1137, 1998). Tissue or cell homogenates expressing BK receptors are incubated with [$^3$H]-BK (0.1-2 nM final) in the presence or absence of unlabeled BK (1-10 μM final) to define total and non-specific binding, respectively, in microtiter plates or polypropylene assay tubes in a final assay volume of 0.25-1 mL in a buffer solution containing a cocktail of peptidase inhibitors. Test compounds (at various concentrations) are substituted for unlabeled BK. After a 60 min incubation on ice the assay is rapidly terminated by vacuum filtration and receptor bound radioactivity determined by β-scintillation counting (Sharif and Whiting, *Neurochem. Int.* 18: 89-96, 1991).

All reagent and test compound additions to the assay plates are made using Biomek 2000 robotic workstations (Beckman Instruments, Fullerton, Calif.). The data are then analyzed using an automated, iterative, sigmoidal curve-fitting computer program to obtain the potency and intrinsic activities of the test agents as previously described (Sharif et al. *J. Pharmacol. Exp. Ther.* 286: 1094-1102, 1998; Sharif et al. *Invest Opthalmol. Vis. Sci.* 39:2562-2571, 1998; Kelly et al. *J. Pharmacol. Exp. Ther.* 304: 238-245, 2003). The sources of other materials and reagents for such assays can be found in Sharif and Whiting, *Neurochem. Int.* 18: 89-96, 1991. High affinity displacers of [$^3$H]-BK in these assays would exhibit inhibition constants ($IC_{50}$s; i.e. antagonists compound concentration inhibiting 50% of the maximum agonist effect) in the range of 0.01-100 nM and thus constitute potential BK agonists worthy of pursuit for testing in specific cell-based functional assays as described below.

Functional Assays

Agents that can specifically activate native or recombinant BK receptors (preferably human $B_2$ types) present in isolated animal or human tissues [strips or rings] (Sharif and Whiting, *Neurochem. Int.* 18: 89-96, 1991; Rizzi et al. *Naunyn-Schmiedeberg Arch. Pharmacol.* 360: 361-367, 1999), in cultured cells of animal or human tissue source (Sharif et al., *Neurosci. Lett.* 86: 279-283, 1988; Sharif and Whiting, *Neurochem. Res.* 12: 1313-1320, 1993), especially primary or immortalized ocular cells involved in aqueous humor dynamics such as human trabecular meshwork (h-TM) (Sharif and Xu, *Exp. Eye Res.* 63: 631-637, 1996), human ciliary muscle cells (h-CM; Sharif et al. *J. Ocular Pharmacol. Ther.* 19: 437-455, 2003), non-pigmented ciliary epithelial (NPE; Crider and Sharif, *J. Ocular Pharmacol. Ther.* 18: 221-230, 2002) can be discovered by measuring second messengers such as inositol phosphates (Sharif et al., *Neurosci. Lett.* 86: 279-283, 1988; Sharif and Whiting, *Neurochem. Res.* 12: 1313-1320, 1993), intracellular $Ca^{2+}$ ($[Ca^{2+}]_i$) (Kelly and Sharif, *J. Pharmacol. Expt. Ther.* 317:1254-1261, 2006), cAMP (Crider and Sharif, J. Ocular Pharmacol. Ther. 18: 221-230, 2002) and cGMP (Zhang et al., *Exp. Eye Res.* 21: 748-756, 2001) produced after stimulation of the BK receptor using well documented procedures.

BK agonists can more specifically be discovered using human or Chinese hamster ovary cell-lines expressing recombinant human $B_2$ BK receptors and measuring one or more of the second messengers (inositol phosphates (IPs); $[Ca^{2+}]_i$; cGMP, cAMP) in the presence or absence of the test agent. An agent that stimulates the production of one or more of these second messengers would be classified as a BK agonist as previously demonstrated (Sharif et al., *Neurosci. Lett.* 86: 279-283, 1988; Sharif and Whiting, *Neurochem. Res.* 12: 1313-1320, 1993; Aramori et al., *Mol. Pharmacol.* 52: 16-20, 1997; Asano et al., *Br. J. Pharmacol.* 124: 441-446, 1998; Sawada et al., *J. Med. Chem.* 47: 2853-2863, 2004). In addition, the pharmacological characteristics of specific BK agonists can be further defined using the latter techniques and reagents and other BK agonists and antagonists (Sharif et al., *Neurosci. Lett.* 86: 279-283, 1988; Sharif and Whiting, *Neurochem. Res.* 12: 1313-1320, 1993; Aramori et al., *Mol. Pharmacol.* 52: 16-20, 1997; Asano et al., *Br. J. Pharmacol.* 124: 441-446, 1998; Sawada et al., *J. Med. Chem.* 47: 2853-2863, 2004; Abe et al., *J. Med. Chem.* 41: 4053-4061, 1998; Sawada et al., *J. Med. Chem.* 47: 2853-2863, 2004). It is important to demonstrate agonist activity of BK agonists in human ocular cells known to be involved in aqueous humor dynamics in order to demonstrate the presence of the target receptors in these target cells and to correlate the in vitro actions of these compounds with their IOP-lowering activity.

Functional Assay Using Isolated Tissues

A functional assay involving contraction of isolated tissues in organ baths in response to BK or test compounds can be performed as previously described (Walestedt et al. *Eur. J. Pharmacol.* 106: 577-583, 1985; Sharif and Whiting, *Neurochem. Int.* 18: 89-96, 1991; Rizzie et al., *Naunyn-Schmiedeberg Arch. Pharmacol.* 360: 361-367, 1999). Thus, longitudinal fundus muscle strips (1.5×20 mm), umbilical cord or blood vessel spiral strips, or guinea pig ileum, or bovine or human trabecular meshwork (Wiederholt et al. *Invest. Opthalmol. Vis. Sci.* 38: 1883-1892, 1997) or ciliary muscle or iris (Walestedt et al. *Eur. J. Pharmacol.* 106: 577-583, 1985) other tissue expressing endogenous BK receptors are mounted in 25 mL organ baths containing oxygenated (95% $O_2$/5% $CO_2$) Krebs buffer solution at 37° C. The Krebs buffer solution is composed of the following (mM): $NaCl_2$ 118; KCl 4.8; $CaCl_2$ 2.5; $KH_2PO_4$ 1.2; $NaHCO_3$ 25; $MgSO_4$ 2.0; dextrose 10 and flurbiprofen 0.003 (pH 7.4).

Longitudinal isometric tension can be recorded via a FTO3 transducer and displayed on a Polyview Computer software analyzer (resting tension=1 gm). Tissues are allowed to equilibrate for 30-45 min after which the test agents are added in ascending concentrations, the maximal response being allowed to reach a plateau before each subsequent addition (cumulative contractile concentration-responses) (Sharif and Whiting, *Neurochem. Int.* 18: 89-96, 1991). In order to verify the agonist activity being mediated via BK receptors, the BK antagonists are allowed to be present in the bathing buffer for 30 min before the purported agonist is tested. Results for agonist are expressed as gram tension developed and as % maximum response of each of the compounds relative to BK (1 μM; positive control; set at 100%). A suitable BK antagonist (10 μM), such as HOE-140 or WIN-64338 or others (see U.S. Pat. No. 6,500,831; Hall, J. M., *Pharmacol. Ther.*, 56, 131-190, 1992; and Leeb-Lundberg et al., *Pharmacol. Rev.* 57: 27-77, 2005; Abe et al. *J. Med. Chem.* 41: 4053-4061, 1998; Sawada et al., *J. Med. Chem.* 47: 2853-2863, 2004), should almost completely block the effect of any BK agonist or test agent active in this assay. Agonists active in these assays should exhibit at least a potency ($EC_{50}$ value, i.e. agonist compound concentration producing 50% of the maximum response) of 0.01-1,000 nM to be considered suitable for the current embodiments. However, BK agonists with lower potencies than the above limits, whether partial or full agonists, can still be considered useful ocular hypotensive agents and may be useful as such.

Functional Assay Measuring [$^3$H]-Inositol Phosphates or Inositol Phosphate-1 Production in Cultured Cells A functional assay involving measurement of the second messengers inositol phosphates in human ocular cells involved in IOP-modulation, including h-TM, h-CM or NPE cells, can be performed as previously described (Sharif et al., *Neurosci. Lett.* 86: 279-283, 1988; Sharif and Whiting, *Neurochem. Res.* 12: 1313-1320, 1993; Sharif and Xu, *Exp. Eye Res.* 63: 631-637, 1996; Sharif et al. *J. Ocular Pharmacol. Ther.* 19: 437-455, 2003; Sharif et al., *J. Ocular Pharmacol. Ther.* 18: 141-162, 2002). In addition, cells expressing human recombinant $B_2$ and $B_1$ BK receptors can be used for such studies. Thus, phospholipase C-mediated phosphoinositide (PI) turnover assays involve the measurement of agonist-stimulated production of [$^3$H]-inositol phosphates ([$^3$H]-IPs) by anion-exchange chromatography. Confluent h-TM, h-CM or other relevant human or animal ocular or non-ocular cells or cells expressing recombinant (preferably human) BK receptors cultured in 24- or 48-well culture plates are exposed for 24 hrs at 37° C. to 2-3 μCi [$^3$H]-myo-inositol (18-20 Ci/mmol; Amersham Pharmacia Biotech, Arlington Heights, Ill.) in 1.0 ml of the respective serum-free medium in order to label inositol-containing cell membrane phospholipids.

Cells are then rinsed once with DMEM/F-12 culture medium containing 10 mM LiCl prior to incubation with the test compound at various concentrations (or solvent vehicle as the control) in 0.5 ml of the same medium for 1 h at 37° C. After this time, the medium is aspirated and 1 ml of ice-cold 0.1 M formic acid is added. When the antagonist effects of BK antagonists are studied, these are added to the cells 15 min prior to exposure to the agonists and the incubation continued for another hour. The anion exchange chromatographic separation of [$^3$H]-IPs on an AG-1-X8 column is performed as previously with sequential washes with $H_2O$ and 50 mM ammonium formate, followed by elution of the total [$^3$H]-IPs fraction with 1.2 M ammonium formate containing 0.1 M formic acid. Each eluate (4 ml) is collected into a scintillation vial, mixed with 15 ml scintillation fluid, and the total [$^3$H]-IPs determined by scintillation counting on a Beckman LS6000 β-counter (Beckman Instruments, Fullerton, Calif.). All reagent and test compound additions to the assay plates are made using Biomek 2000 robotic workstations (Beckman Instruments, Fullerton, Calif.).

In the above protocol, ocular cells can be substituted with cells from animal tissues or cells that express recombinant BK receptors (Aramori et al., *Mol. Pharmacol.* 52: 16-20, 1997; Asano et al., *Br. J. Pharmacol.* 124: 441-446, 1998; Sawada et al., *J. Med. Chem.* 47: 2853-2863, 2004). The data are then analyzed using an automated, iterative, sigmoidal curve-fitting computer program to obtain the potency and intrinsic activities of the test agents as previously described (Sharif et al. *J. Pharmacol. Exp. Ther.* 286: 1094-1102, 1998; Sharif et al. *Invest. Opthalmol. Vis. Sci.* 39:2562-2571, 1998; Kelly et al. *J. Pharmacol. Exp. Ther.* 304: 238-245, 2003). The sources of materials and reagents for such assays can be found in the references cited above. Compounds that significantly and in a concentration-dependent manner stimulate the production of [$^3$H]-IPs above the basal levels can be classified as BK agonists. Agonists active in these assays should exhibit at least a potency ($EC_{50}$ value) of 0.01-1,000 nM to be considered suitable for the current embodiments. However, BK agonists with lower potencies than the above limits, whether partial or full agonists, can still be considered useful ocular hypotensive agents and may be useful as such. A suitable BK antagonist (10 µM), such as HOE-140 or WIN-64338 or others (see U.S. Pat. No. 6,500,831; Hall, J. M., *Pharmacol. Ther.*, 56, 131-190, 1992; Leeb-Lundberg et al., *Pharmacol. Rev.* 57: 27-77, 2005; Abe et al. *J. Med. Chem.* 41: 4053-4061, 1998; Sawada et al., *J. Med. Chem.* 47: 2853-2863, 2004), should almost completely block the effect of any BK agonist or test agent active in this assay.

Another method for measuring inositol phosphate-1 (IP1) generated endogenously by PI hydrolysis involves a homogeneous time-resolved fluorescence (HTRF®) detection method using cells expressing endogenous BK receptors or Chinese hamster ovary cells transfected with human BK receptors. The cells are suspended in IP1 stimulation buffer containing Hepes 10 mM, $CaCl_2$ 1 mM, $MgCl_2$ 0.5 mM, KCl 4.2 mM, NaCl 146 mM, Glucose 5.5 mM, LiCl 50 mM pH 7.4, then distributed in microplates at a density of 40,000 cells/well ($B_2$ receptor assays) or 30,000 cells/well ($B_1$ receptor assays). Test compounds are added to the cells at various concentrations and incubated for 20 min at 37° C. Reference agonist bradykinin is added at a final concentration of 1 µM. For basal control measurements, separate assay wells do not contain bradykinin. Following the 20 min incubation at 37° C., the cells are lysed and the fluorescence acceptor (D2-labeled IP1) and fluorescence donor (anti-IP1 antibody labeled with europium cryptate) are added. After 60 min at room temperature, the fluorescence transfer is measured at $\lambda ex=337$ nm and $\lambda em=620$ and 665 nm using a microplate reader. The results are expressed as a percent of the control response to 1 µM bradykinin.

Functional Assay Measuring of $[Ca^{2+}]_i$ Mobilization in Cultured Cells

A functional assay involving measurement of $[Ca^{2+}]_i$ mobilized by BK or test compounds in h-TM, h-CM or other relevant human or animal ocular or non-ocular cells or cells expressing recombinant (preferably human) BK receptors can be performed as previously described (Sharif et al. *J. Ocular Pharmacol. Ther.* 19: 437-455, 2003; Sharif et al., *J. Ocular Pharmacol. Ther.* 18: 141-162, 2002; Sharif et al. *Invest. Opthalmol. Vis. Res.* 47: 4001-4019, 2006; Sharif et al., *J. Ocular Pharmacol. Ther.* 22: 291-309, 2006). Cells expressing recombinant BK receptors can be also used (Aramori et al., *Mol. Pharmacol.* 52: 16-20, 1997; Asano et al., *Br. J. Pharmacol.* 124: 441-446, 1998; Sawada et al., *J. Med. Chem.* 47: 2853-2863, 2004). Thus, BK-induced $[Ca^{2+}]_i$ mobilization can be studied using the Fluorescence Imaging Plate Reader (FLIPR) instrument (Kelly and Sharif, *J. Pharmacol. Expt. Ther.* 317: 1254-1261, 2006). Cells expressing BK receptors are seeded at a density of about 20,000 cells/well in a black-wall, 96-well tissue culture plates and grown for 2 days.

On the day of the experiment, one vial of FLIPR Calcium Assay Kit dye is re-suspended in 50 mL of a FLIPR buffer consisting of Hank's Balanced Salt Solution (HBSS), 20 mM HEPES, and 2.5 mM probenecid, pH 7.4. Cells are loaded with the calcium-sensitive dye by addition of an equal volume (50 µL) to each well of the 96-well plate and incubated with dye for 1 h at 23° C. After this time, the test compound plate and cell plate are placed in the FLIPR instrument. At the beginning of an experimental run, a signal test is performed to check the basal fluorescence signal from the dye-loaded cells and the uniformity of the signal across the plate. The basal fluorescence is adjusted between 8000-12000 counts by modifying the exposure time, the camera F-stop, or the laser power. Instrument settings for a typical assay are the following: laser power 0.3-0.6 W, camera F-stop F/2, and exposure time 0.4 sec. An aliquot (25 µL) of BK solution (positive control) or the test compound is added to the existing 100 µL dye-loaded cells at a dispensing speed of 50 µL/sec.

Fluorescence data are collected in real-time at 1.0 sec intervals for the first 60 secs and at 6.0 sec intervals for an additional 120 secs. Responses are measured as peak fluorescence intensity minus basal and where appropriate are expressed as a percentage of a maximum BK-induced response [$E_{max}$%]. When antagonist studies are performed, the latter are incubated with the cells for 15 minutes prior to the addition of BK or test compound. The data are then analyzed using an automated, iterative, sigmoidal curve-fitting computer program to obtain the potency and intrinsic activities of the test agents as previously described (Sharif et al. *J. Pharmacol. Exp. Ther.* 286: 1094-1102, 1998; Sharif et al. *Invest. Opthalmol. Vis. Sci.* 39:2562-2571, 1998; Kelly et al. *J. Pharmacol. Exp. Ther.* 304: 238-245, 2003). The sources of materials and reagents for such assays can be found in the references cited above. Compounds that significantly and in a concentration-dependent manner stimulate the mobilization of $[Ca^{2+}]_i$ above the basal levels can be classified as BK agonists. Test compounds that exhibit functional potencies ($EC_{50}s$) of 0.05-1,000 nM in this assay, whose actions can be blocked by specific BK antagonists (Hall, J. M., *Pharmacol. Ther.*, 56, 131-190, 1992; Sharma, *Gen. Pharmacol.*, 24, 267-274, 1993; Abe et al., *J. Med. Chem.* 41: 4053-4061, 1998; Sawada et al., *J. Med. Chem.* 47: 2853-2863, 2004), can be considered suitable BK agonists. Agonists active in these assays should exhibit at least a potency ($EC_{50}$ value) of 0.01-1,000 nM to be considered suitable for the current embodiments. However, BK agonists with lower potencies than the above limits, whether partial or full agonists, can still be considered useful ocular hypotensive agents and may be useful as such. A suitable BK antagonist (10 µM), such as HOE-140 or WIN-64338 or others (see U.S. Pat. No. 6,500,831; Hall, J. M., *Pharmacol. Ther.*, 56, 131-190, 1992; Leeb-Lundberg et al., *Pharmacol. Rev.* 57: 27-77, 2005; Abe et al. *J. Med. Chem.* 41: 4053-4061, 1998; Sawada et al., *J. Med. Chem.* 47: 2853-2863, 2004), should almost completely block the effect of any BK agonist or test agent active in this assay.

Functional Assay Measuring cGMP Production in Cultured Cells

A functional assay to discover BK agonists may involve the measurement of cGMP production (Pang et al., *Invest. Opthalmol. Vis. Sci.* 37: 1724-1731, 1996) in cells isolated from human or animal ocular or non-ocular tissues, or cells expressing recombinant (preferably human) BK receptors. Cells expressing BK receptors are seeded in 48-wells culture plates and allowed to reach confluence. After this time the cells are rinsed twice with 0.5 ml Dulbeco's modified Eagle's medium (DMEM)/F-12. The cells are then pre-incubated for 20 minutes with 1.0 mM of the phosphodiesterase inhibitor 3-isobutyl-1-methylxanthine (IBMX; Sigma-Aldrich, St. Louis, Mo.) at 23° C. after which BK or test compound (various concentrations ranging from 0.01 nM to 10 µM) is added and the incubation allowed to proceed for another 15 minutes at 23° C. After aspiration of the reaction medium, ice cold 0.1 M acetic acid (150 µL pH 3.5) is added for the termination of cGMP synthesis and cell lysis. Finally, ice cold 0.1 M sodium acetate (220 µL, pH 11.5-12.0) is added to neutralize the samples before analysis by a enzyme immunosorbant assay kit for cGMP (Amersham Pharmacia Biotech, Piscataway, N.J.) according to the manufacturer's instructions using a robotic workstation (Biomek 2000; Beckman Instrument, Fullerton, Calif.).

When the effects of BK antagonists are investigated the latter are present in the assay mixture during the 20 min pre-incubation step. Test compounds that exhibit functional potencies ($EC_{50}$s) of 0.01-1,000 nM in this assay, whose actions can be blocked by specific BK antagonists (Hall, J. M., *Pharmacol. Ther.*, 56, 131-190, 1992; Sharma, *Gen. Pharmacol.*, 24, 267-274, 1993; Abe et al., *J. Med. Chem.* 41: 4053-4061, 1998; Sawada et al., *J. Med. Chem.* 47: 2853-2863, 2004), can be considered suitable BK agonists. However, BK agonists with lower potencies than the above limits, whether partial or full agonists, can still be considered useful ocular hypotensive agents and may be useful as such. A suitable BK antagonist (10 μM), such as HOE-140 or WIN-64338 or others (see U.S. Pat. No. 6,500,831; Hall, J. M., *Pharmacol. Ther.*, 56, 131-190, 1992; Leeb-Lundberg et al., *Pharmacol. Rev.* 57: 27-77, 2005; Abe et al. *J. Med. Chem.* 41: 4053-4061, 1998; Sawada et al., *J. Med. Chem.* 47: 2853-2863, 2004), should almost completely block the effect of any BK agonist or test agent active in this assay.

Functional Assay Measuring cAMP Production in Cultured Cells

A functional assay to discover BK agonists may involve the measurement of cAMP production (Crider and Sharif, *J. Ocular Pharmacol. Ther.* 18: 221-230, 2002) in cells isolated from human or animal ocular or non-ocular tissues, or cells expressing recombinant (preferably human) BK receptors. Cells expressing BK receptors are seeded in 48-wells culture plates and allowed to reach confluence. After this time the cells are rinsed twice with 0.5 ml Dulbeco's modified Eagle's medium (DMEM)/F-12. The cells are then pre-incubated for 20 minutes with 1.0 mM of the phosphodiesterase inhibitor 3-isobutyl-1-methylxanthine (IBMX; Sigma-Aldrich, St. Louis, Mo.) at 23° C. after which BK or test compound (various concentrations ranging from 0.01 nM to 10 μM) is added and the incubation allowed to proceed for another 15 minutes at 23° C. After aspiration of the reaction medium, ice cold 0.1 M acetic acid (150 μL, pH 3.5) is added for the termination of cAMP synthesis and cell lysis. Finally, ice cold 0.1 M sodium acetate (220 μL, pH 11.5-12.0) is added to neutralize the samples before analysis by an enzyme immunosorbant assay kit for cAMP (Amersham Pharmacia Biotech, Piscataway, N.J.) according to the manufacturer's instructions using a robotic workstation (Biomek 2000; Beckman Instrument, Fullerton, Calif.).

When the effects of BK antagonists are investigated the latter are present in the assay mixture during the 20 min pre-incubation step. Test compounds that exhibit functional potencies ($EC_{50}$s) of 0.01-1,000 nM in this assay, whose actions can be blocked by specific BK antagonists (Hall, J. M., *Pharmacol. Ther.*, 56, 131-190, 1992; Sharma, *Gen. Pharmacol.*, 24, 267-274, 1993; Abe et al., *J. Med. Chem.* 41: 4053-4061, 1998; Sawada et al., *J. Med. Chem.* 47: 2853-2863, 2004), can be considered suitable BK agonists. Agonists active in these assays should exhibit at least a potency ($EC_{50}$ value) of 0.01-1,000 nM to be considered suitable for the current embodiments. However, BK agonists with lower potencies than the above limits, whether partial or full agonists, can still be considered useful ocular hypotensive agents and may be useful as such. A suitable BK antagonist (10 μM), such as HOE-140 or WIN-64338 or others (see U.S. Pat. No. 6,500,831; Hall, J. M., *Pharmacol. Ther.*, 56, 131-190, 1992; Leeb-Lundberg et al., *Pharmacol. Rev.* 57: 27-77, 2005; Abe et al. *J. Med. Chem.* 41: 4053-4061, 1998; Sawada et al., *J. Med. Chem.* 47: 2853-2863, 2004), should almost completely block the effect of any BK agonist or test agent active in this assay.

A functional assay to discover BK agonists may involve the measurement of inhibition of forskolin-induced cAMP generation in cultured cells expressing human recombinant $B_2$-receptors or other cell types (Meini et al. *Brit. J. Pharmacol.* 143: 938-941, 2004; Sharif et al. *J. Pharmac. Pharmacol.* 56: 1267-1274, 2004). The assays are performed as described directly above except that the test agent is added along with IBMX during the pre-incubation period. The assay is initiated with the addition of forskolin (10 μM final), a direct activator of adenylyl cyclase, and allowing the incubation to continue for 15 min at 23° C. After this time the assay is terminated and the cAMP quantified as described above. Test compounds that exhibit functional potencies ($EC_{50}$s) of 0.01-1,000 nM in this assay, whose actions can be blocked by specific BK antagonists (Hall, J. M., *Pharmacol. Ther.*, 56, 131-190, 1992; Sharma, *Gen. Pharmacol.*, 24, 267-274, 1993; Abe et al., *J. Med. Chem.* 41: 4053-4061, 1998; Sawada et al., *J. Med. Chem.* 47: 2853-2863, 2004), can be considered suitable BK agonists. Test agents should exhibit at least a potency ($EC_{50}$ value) of 0.01-1,000 nM to be considered suitable for the current embodiments. However, BK agonists with lower potencies than the above limits, whether partial or full agonists, can still be considered useful ocular hypotensive agents and may be useful as such. A suitable BK antagonist (10 μM), such as HOE-140 or WIN-64338 or others (see U.S. Pat. No. 6,500,831; Hall, *Pharmacol. Ther.*, 56, 131-190, 1992; Leeb-Lundberg et al., *Pharmacol. Rev.* 57: 27-77, 2005; Abe et al. *J. Med. Chem.* 41: 4053-4061, 1998; Sawada et al., *J. Med. Chem.* 47: 2853-2863, 2004), should almost completely block the effect of any BK agonist or test agent active in this assay.

Functional Assay Measuring Prostaglandin $E_2$ Production in Cultured Cells

A functional assay to discover BK agonists may involve the measurement of prostaglandin $E_2$ ($PGE_2$) production (Wiernas et al. *Brit. J. Pharmacol.* 123: 1127-1137, 1998), for instance, in cells isolated from human or animal ocular or non-ocular tissues, or cells expressing recombinant (preferably human) BK receptors. Cells expressing BK receptors are seeded in 48-wells culture plates and allowed to reach confluence. After this time the cells are rinsed twice with 0.5 mL of phosphate buffered saline and incubated with the test agent made up in 0.5 mL Dulbeco's modified Eagle's medium (DMEM)/F-12 for 1 h at 37° C. After this time the assay is terminated by placing the assay plates on ice and by the addition of 100 μL of a cell-lysis reagent supplied with the $PGE_2$ radioimmunoassay (RIA) kit (Amersham Pharmacia Biotech, Arlington Heights, Ill.). All reagents and standards supplied in the RIA kit are prepared and the RIA performed according to the manufacturer's instructions. Assay buffer, diluted $PGE_2$ standard and supernatant from the cell-based experiment (diluted 1:100 v/v) are then pipetted into appropriate tubes as specified in the kit instructions. The tracer solution (100 μL) is then added to each tube and mixed, followed by 100 μL antiserum to the appropriate tubes and thoroughly mixed. All tubes are then incubated overnight at 4° C.

After this incubation, all tubes are placed in an ice-bath and 1 ml cold precipitating reagent supplied in the kit is added to the tubes, the content mixed and incubated for 25 min at 4° C. The tubes are centrifuged in a refrigerated centrifuge at 2,000×g force for 30 min. The supernatants of all tubes are decanted as specified in the kit instructions and the RIA samples analyzed on a gamma-counter. The levels of $PGE_2$ generated by the test agent are then quantified in comparison with the $PGE_2$-standard curve. Dose-response data for the test agent are constructed and the potency and intrinsic activity determined as described above for other assays. Test compounds that exhibit functional potencies ($EC_{50}$s) of 0.01-1,000 nM in this assay, whose actions can be blocked by specific BK antagonists (Hall, *Pharmacol. Ther.*, 56, 131-190, 1992; Sharma, *Gen. Pharmacol.*, 24, 267-274, 1993; Abe et al., *J. Med. Chem.* 41: 4053-4061, 1998; Sawada et al., *J. Med. Chem.* 47: 2853-2863, 2004), can be considered suitable BK agonists. Test agents that stimulate $PGE_2$ production in such assays can be classified as BK agonists and should exhibit at least a potency ($EC_{50}$ value) of 0.01-1,000 nM to be considered suitable for the current embodiments. However, BK agonists with lower potencies than the above limits, whether partial or full agonists, can still be considered useful ocular hypotensive agents and may be useful as such. A suitable BK antagonist (10 µM), such as HOE-140 or WIN-64338 or others (see U.S. Pat. No. 6,500,831; Hall, J. M., *Pharmacol. Ther.*, 56, 131-190, 1992; Leeb-Lundberg et al., *Pharmacol. Rev.* 57: 27-77, 2005; Abe et al. *J. Med. Chem.* 41: 4053-4061, 1998; Sawada et al., *J. Med. Chem.* 47: 2853-2863, 2004), should almost completely block the effect of any BK agonist or test agent active in this assay.

Functional Assay Measuring Nitric Oxide (NO) Production in Cultured Cells

A functional assay to discover BK agonists may involve the measurement of nitric oxide (NO) production using a fluorescent probe (Leikert et al., *FEBS Lett.*, 506: 131-134, 2001; Strijdom et al., *J. Mol. Cell. Cardiol.*, 37: 897-902, 2004) or an NO-selective electrochemical sensor (Berkels et al., *J. Appl. Physiol.* 90: 317-320, 2001) in cells isolated from human or animal ocular or non-ocular tissues, or cells expressing recombinant (preferably human) BK receptors. The measurement of NO by using a the fluorescent probe 4,5-diaminoflurescein-2-diacetate (DAF-2) is based on the reaction of DAF-2 with NO in the presence of $O_2$ under neutral pH, yielding the highly fluorescent triazolofluorescein (DAF-2T). For this assay, cells expressing BK receptors are seeded in 24- or 48-wells culture plates and allowed to reach confluence. After rinsing with phosphate buffered saline the cells were pre-incubated with L-arginine (100 µM final) for 5 min at 37° C. in the dark. After this time, A23187 (1 µM) and DAF-2 (0.1 µM) are added to the cells and the incubation continued for another 5 min at 37° C. in the dark. The fluorescence of the supernatants can then be measured at 23° C. using a spectrofluorimeter with excitation wavelength set at 495 nm and emission wavelength at 515 nm and band width set at 10 nm for both excitation and emission under high sensitivity setting. A standard curve for the DAFF-2T fluorescence intensity and a curve correlating increasing amounts of NO (released from the NO-donor NOC-9 in the presence of EA.hy926 cells) to the fluorescence intensity obtained after addition of 0.1 µM DAF-2 is also generated to help quantify the amount of NO produced during the experiments with the test agents. A commercial kit to measure NO produced by BK receptor activation is also available from Promega (Madison, Wis.). The data are analyzed and compound potencies determined as described for other assays above. Test agents that stimulate NO production in such assays can be classified as BK agonists and should exhibit at least a potency ($EC_{50}$ value) of 0.01-1,000 nM to be considered suitable for the current embodiments. However, BK agonists with lower potencies than the above limits, whether partial or full agonists, can still be considered useful ocular hypotensive agents and may be useful as such. A suitable BK antagonist (10 µM), such as HOE-140 or WIN-64338 or others (see U.S. Pat. No. 6,500,831; Hall, *Pharmacol. Ther.*, 56, 131-190, 1992; Leeb-Lundberg et al., *Pharmacol. Rev.* 57: 27-77, 2005; Abe et al. *J. Med. Chem.* 41: 4053-4061, 1998; Sawada et al., *J. Med. Chem.* 47: 2853-2863, 2004), should almost completely block the effect of any BK agonist or test agent active in this assay.

Functional Assay Involving Measurement of MMP Activity

As with FP-class prostanoids, the IOP-lowering effects of BK may involve the stimulation of production of various MMPs that in turn digest the extracellular matrix (ECM) to promote outflow and thus lower IOP (Mietz et al., *Invest. Opthalmol. Vis. Sci.* 44: 5182-5188, 2003; Webb et al., *J. Ocular Pharmacol. Ther.* 22: 310-316, 2006). Cells isolated from human or animal ocular or non-ocular tissues, or cells expressing recombinant (preferably human) BK receptors are seeded in 48-wells culture plates and allowed to reach confluence. After this time the cells are rinsed twice with 0.5 ml of phosphate buffered saline and incubated with the test agent made up in 0.5 ml Dulbeco's modified Eagle's medium (DMEM)/F-12 for 1 h at 37° C. BK (100 nM) can be used a positive control compound. After this time the supernatant from each well is concentrated 20-fold (Centricon Concentrators; Millipore Corp., Bedford, Mass.). Equivalent volumes of media are then loaded onto 12% sodium dodicyl sulfate polyacrylamide gels, where the secreted proteins are separated according to their molecular weights by standard SDS-polyacrylamide gel electrophoresis protocols and transferred onto nitrocellulose paper. The level of MMP-1, MMP-2, MMP-3 and MMP-9 is then determined by immunoblot analysis with rabbit polyclonal anti-MMP antibodies. Bands are visualized by the addition of anti-rabbit horseradish peroxidase-conjugated secondary antibodies (New England Biolabs, Inc.; Beverly, Mass.) and enhanced chemiluminescent reagents (Pierce Biotechnology, Inc., Rockford, Ill.) (Mietz et al., *Invest. Opthalmol. Vis. Sci.* 44: 5182-5188, 2003; Webb et al., *J. Ocular Pharmacol. Ther.* 22: 310-316, 2006). BK agonists should stimulate the production of some or all of MMP-1, MMP-2, MMP-3 and MMP-9. Test agents that stimulate MMP production in such assays can be classified as BK agonists and should exhibit at least a potency ($EC_{50}$ value) of 0.01-1,000 nM to be considered suitable for the current embodiments. However, BK agonists with lower potencies than the above limits, whether partial or full agonists, can still be considered useful ocular hypotensive agents and may be useful as such. A suitable BK antagonist (10 µM), such as HOE-140 or WIN-64338 or others (see U.S. Pat. No. 6,500,831; Hall, J. M., *Pharmacol. Ther.*, 56, 131-190, 1992; Leeb-Lundberg et al., *Pharmacol. Rev.* 57: 27-77, 2005; Abe et al. *J. Med. Chem.* 41: 4053-4061, 1998; Sawada et al., *J. Med. Chem.* 47: 2853-2863, 2004), should almost completely block the effect of any BK agonist or test agent active in this assay.

Functional Assay Involving Perfused Anterior Eye Segments

Anterior eye segments obtained from postmortem human, bovine or porcine eyes can be kept alive and can be used to study the effects of test agents on IOP or fluid outflow through the trabecular meshwork and Schlemms' canal (Erickson-Lamey et al., *Curr. Eye Res.* 7: 799-807, 1988; Vaajanen et al. *J. Ocular Pharmacol. Ther.* 23: 124-131, 2007). The postmortem eyes are placed in DMEM containing 50 U/ml penicillin, 50 µg/mL streptomycin, and 5 µg/mL amphotericin B prior to dissection under sterile conditions. Eyes are bisected at the equator and the anterior chamber transferred to a petri dish. The lens is removed and the remaining choroid, iris, and ciliary body gently teased away. Once isolated, the corneaoscleral shell is attached to a perfusion chamber and perfused with DMEM supplemented with 50 U/mL penicillin and 50 µg/mL streptomycin. The entire perfusion apparatus is maintained in an incubator at 37° C. and 5% $CO_2$ in air. Perfusion pressure for standard perfusion is maintained at a constant level of 10 mmHg, and rate of fluid outflow monitored continuously (i.e. by means of a Model ACCU 124 analytical balance; Fisher Scientific, Pittsburgh, Pa.) throughout the experiment. The rate of fluid flow is recorded by a computer utilizing Collect XL software (Lab Tronics, Inc; Guelph, Ontario, Canada). Outflow facility can be calculated as the ratio of flow rate to perfusion pressure (µL/min/mmHg).

Preparations are allowed to stabilize overnight (14-16 hr), and baseline facilities are then recorded over the next 40-60 min. Only preparations with stable baselines and baseline facilities ranging from 0.4 to 1.8 µL/min/mmHg are to be used for the experiments. After baseline facility is established, test compounds are introduced into the perfusion system by medium exchange. When segments are treated with a BK antagonist, the latter is included in the perfusion medium during the stabilization period and following media exchange with the test compound. A BK agonist should increase the outflow facility flow and lower IOP. A suitable BK antagonist (10-30 µM), such as HOE-140 or WIN-64338 or others (see U.S. Pat. No. 6,500,831; Hall, *Pharmacol. Ther.*, 56, 131-190, 1992; Leeb-Lundberg et al., *Pharmacol. Rev.* 57: 27-77, 2005; Abe et al. *J. Med. Chem.* 41: 4053-4061, 1998; Sawada et al., *J. Med. Chem.* 47: 2853-2863, 2004), should almost completely block the effect of any BK agonist or test agent active in this assay (Webb et al. *J. Ocular Pharmacol. Ther.* 22: 310-316, 2006). During the course of such studies the perfusates can be analyzed for endogenous agents such as neurotransmitters or MMPs released by the BK agonist in order to study the possible mechanism(s) of action of the agonist.

In Vivo Assays to Detect Ocular Irritation Potential

Test agents are evaluated in animal models of ocular irritation to determine the comfort, overall safety, local side-effects and tolerability of the compound formulation. A single dose of the test agent or vehicle is instilled topically to one or both eyes of five rabbits. Gross observations are made of ocular irritation and behavior for two hours.

Acute Ocular Hyperemia Response in Guinea Pigs

Animals are hand-held under a 3× magnification lamp to score ocular hyperemia (ocular surface redness). Scoring can be accomplished as follows:

Sclera (Bulbar Conjunctiva)

0 Normal appearance of vessels at limbus and rectus muscle

1 Enlargement of vessels normally visible at limbus and rectus muscle

2 Branching of vessels at limbus, new vessels visible

3 New vessels visible in open bulbar conjunctival areas

4 Diffuse redness in open bulbar conjunctival areas

After baseline ocular hyperemia is scored, test compound is instilled in one eye of each of six guinea pigs. A positive control or vehicle is instilled in one eye of each of six additional animals. Ocular hyperemia is scored at 1, 2, 3, and 4 hours post-dose. The % Incidence of hyperemia is calculated as number of scores >2 after drug instillation, divided by the total number of readings (i.e., 24 total number of readings: n=6 eyes scored at 4 time points), times 100. Scores are 0, 1, 2, 3, and 4 in a system devised by this lab based on the visibility of branching in the upper limbal and bulbar conjunctival blood vessels (an indication of blood vessel dilation only).

In Vivo Efficacy and Duration of Action Assays

Agents that can specifically activate native BK receptors present in the anterior chamber of the eye or other ocular tissues/compartments that are intimately involved in aqueous humor dynamics and IOP lowering can be discovered by administering the test compound in a suitable formulation to the eyes of TM-lasered or naturally ocular hypotensive cynomolgus monkeys (or other non-human primates such as rhesus monkeys) and measuring the IOP using a pneumatonometer after light corneal anesthesia with 0.1% proparacaine (Sharif et al. *J. Ocular Pharmacol. Ther.* 17: 305-317, 2001; May et al., *J Pharmacol Exp Ther.* 306: 301-309, 2003; Sharif et al. *Invest. Opthalmol. Vis. Res.* 47: 4001-4010, 2006). In addition, well characterized BK agonists can be applied topical ocularly (or injected into the anterior chamber of the eye or injected intravitreally) to determine their ability to influence IOP in various animal models, especially the ocular hypertensive cynomolgus monkey model as described above. Monkeys may also be anesthetized using intramuscularly administered ketamine to make the topical ocular dosing easier for the investigator (Toris et al. *J. Glaucoma* 14: 70-73, 2005; Toris et al. *J. Ocular Pharmacol. Ther.* 22: 86-92, 2006). However, sedation may change the over efficacy of the test agent.

Some compound classes are known to lower IOP in the rabbit. For these classes single-dose and dose-response studies are conducted in the rabbit. Compounds with acceptable activity are then evaluated in the lasered monkey model.

Acute IOP Response in Rabbit Eyes

IOP is determined with an applanation pneumatonometer after light corneal anesthesia with 0.1% proparacaine. After baseline IOP measurements are taken, one eye of each of 7-10 (or both eyes of 5) rabbits per compound dose is topically dosed with compound. Either the contralateral eye is dosed with vehicle or a separate group of rabbits is used for vehicle control. Subsequent IOP measurements are taken at 0.5, 1, 2, 3, and 4 hours. In cases where the compound has poor ocular bioavailability, the compound may need to be administered intracamerally or intravitreally in order to observe the IOP-lowering efficacy.

IOP Response in Lasered (Hypertensive) Eyes of Cynomolgus Monkeys

Intraocular pressure (IOP) is determined with an Alcon Pneumatonometer (Alcon Laboratories, Inc., Fort Worth, Tex.) after light corneal anesthesia with 0.1% proparacaine. Right eyes are hypertensive as a result of laser trabeculoplasty. After a baseline IOP measurement, test compound is instilled in the right eyes only of 8-10 cynomolgus monkeys. Vehicle is instilled in the right eyes of 5-6 additional animals. Subsequent IOP measurements are taken at 1, 3, and 6 hours. IOP measurements are also taken on left eyes (normotensive and untreated) at each of these time points. The percent change in IOP from baseline is determined for each animal for every IOP measurement (Sharif et al. *J. Ocular Pharmacol. Ther.* 17: 305-317, 2001; May et al., *J Pharmacol Exp Ther.* 306: 301-309, 2003; Sharif et al. *Invest. Opthalmol. Vis. Res.* 47: 4001-4010, 2006). Group mean and standard error of the mean (SEM) are calculated for each time point. A suitable BK antagonist (1% w/v), such as HOE-140 or WIN-64338 or others (see U.S. Pat. No. 6,500,831; Hall, J. M., *Pharmacol. Ther.*, 56, 131-190, 1992; Leeb-Lundberg et al., *Pharmacol. Rev.* 57: 27-77, 2005; Abe et al. *J. Med. Chem.* 41: 4053-4061, 1998; Sawada et al., *J. Med. Chem.* 47: 2853-2863, 2004) dosed topical ocularly 30-90 min prior to the test agent should block the effect of any BK agonist or test agent active in this assay. In cases where the compound of invention has poor ocular bioavailability, the compound may need to be administered intracamerally or intravitreally in order to observe the IOP-lowering efficacy.

All references cited in this application are expressly incorporated by reference herein for any purpose.

Unless otherwise required by context, singular terms used herein shall include pluralities and plural terms shall include the singular.

EXAMPLES

Example 1

Bradykinin and its Receptor mRNAs are Expressed in Relevant Human Ocular Tissues and Cells Molecular biological techniques were used to demonstrate the presence of mRNAs for the precursor protein for BK (kininogen) and the two receptors for BK (B1- and B2-types) in numerous human ocular tissues and cells including relatively high levels in the most relevant ones involved in aqueous humor dynamics and IOP modulation, namely TM and CB (Tables 1 and 2).

TABLE 1

Microarray Analysis of BK Precursor (Kinnogen) and BK Receptor mRNAs Expression in Normal Human Ocular Tissues Normalized Levels of mRNAs (normalized expression based on GC-RMA algorithm)

| Tissue | Kininogen | $B_1$-Receptor | $B_2$-Receptor |
|---|---|---|---|
| Trabecular meshwork | 0.92 | 0.5 | 1.04 |
| Ciliary body | 0.9 | 0.9 | 1.09 |
| Optic nerve head | 1.14 | 0.53 | 0.96 |
| Sclera | 0.63 | 0.45 | 2.47 |
| Iris | 0.69 | 0.5 | 1.1 |
| Lens | 0.65 | 0.42 | 0.72 |
| Optic nerve | 0.64 | 0.42 | 0.61 |

TABLE 1-continued

Microarray Analysis of BK Precursor (Kinnogen) and BK Receptor mRNAs Expression in Normal Human Ocular Tissues Normalized Levels of mRNAs (normalized expression based on GC-RMA algorithm)

| Tissue | Kininogen | $B_1$-Receptor | $B_2$-Receptor |
|---|---|---|---|
| Choroid | 0.63 | 0.42 | 0.91 |
| Cornea | 0.61 | 0.48 | 1.6 |
| Retina | 0.49 | 0.43 | 0.54 |

TABLE 2

Microarray Analysis of BK Precursor (Kinnogen) and BK Receptor mRNAs Expression in Normal and Glaucomatous Human TM Cells and Tissues Normalized Levels of mRNAs (normalized expression based on GC-RMA algorithm)

| | Normal TM Cells | Glaucomatous TM Cells | Normal TM Tissue | Glaucomatous TM Tissue |
|---|---|---|---|---|
| Kininogen | 1.0 | 0.62 | 1.0 | 2.48 |
| $B_1$-receptor | 1.0 | 0.91 | 1.0 | 0.9 |
| $B_2$-receptor | 1.0 | 2.02 | 1.0 | 0.94 |

Since the up-regulation of the cytokine transforming growth factor-$\beta_2$ (TGF-$\beta_2$) has been implicated as a possible causative factor in the etiology of ocular hypertension and glaucoma (Tripathi et al., *Exp. Eye Res.*, 59: 723-727, 1994; Fuchshofer et al., *Exp. Eye Res.* 77: 757-765, 2003), it was of significance that exogenous exposure of h-TM cells derived from normal and glaucomatous h-TM tissues to TGF-$\beta_2$ for 90 min or 16 hrs resulted in down-regulation of $B_2$-receptor mRNA in normal h-TM cells (also in glaucomatous h-TM cells at the 16 hr time-point) (Table 3). In contrast, the $B_1$-receptor mRNA was up-regulated after 90 min but down-regulated after 16 hrs treatment with TGF-$\beta_2$ in glaucomatous h-TM cells (Table 3).

TABLE 3

Microarray Analysis of BK Receptor mRNAs Expression in Normal and Glaucomatous in TGF$_{\beta2}$-Treated Human TM Cells Normalized Levels of mRNAs (normalized expression based on GC-RMA algorithm mean ± SEM)

| | Normal h-TM Cells | | | Glaucomatous h-TM Cells | | |
|---|---|---|---|---|---|---|
| | Control | TGF$_{\beta2}$-Treated (after 1.5 hr) | TGF$_{\beta2}$-Treated (after 16 hr) | Control | TGF$_{\beta2}$-Treated (after 1.5 hr) | TGF$_{\beta2}$-Treated (after 16 hr) |
| $B_1$-receptor | nd | nd | nd | 0.99 ± 0.58 | 1.54 ± 0.09 ($p < 0.01$) | 0.53 ± 0.05 ($p < 0.02$) |
| $B_2$-receptor | 0.99 ± 0.06 | 0.68 ± 0.05 ($p < 0.04$) | 0.14 ± 0.11 ($p < 0.08$) | 0.99 ± 0.04 | 0.97 ± 0.06 ($p < 0.69$) | 0.24 ± 0.06 ($p < 0.02$) |

GC-RMA = gene chip robust multi-array analysis;
h-TM = human trabecular meshwork;
nd = not determined.

Example 2

Functional Bradykinin Receptors are Expressed by Relevant Human Ocular Tissues and Cells While the detection of mRNAs for kininogen and both $B_1$- and $B_2$-receptors and their modulation by TGF-$\beta_2$ was considered important, the demonstration of the existence of the functional BK receptor proteins in the IOP-modulating cells was critical. Accordingly, we discovered and pharmacologically characterized $B_2$-receptor proteins in h-TM, h-CM and h-NPE cells coupled to the enzyme phospholipase C. The activation of these $B_2$-receptors by BK and BK-analogs resulted in the generation of intracellular second messengers, inositol phosphates, which in turn mobilized $[Ca^{2+}]_i$ in these cells (Table 4; FIG. 1).

TABLE 4

Functional Agonist Potency of BK- and BK-related Peptide-induced $[Ca^{2+}]_i$ Mobilization in Human Ocular TM, CM, and NPE Cells

| Peptide | Agonist Potency (EC$_{50}$; nM) and Intrinsic Activity (E$_{max}$, % max relative to BK) | | |
|---|---|---|---|
| | h-TM Cells | h-CM Cells | h-NPE Cells |
| BK (SEQ ID NO: 1) | 0.8 ± 0.2 | 2.4 ± 0.2 | 6.3 ± 1.4 |
| Hyp$^3$-BK (SEQ ID NO: 11) | 0.9 ± 0.3 | 2.2 ± 0.2 | 6.0 ± 0.6 |
| Lys-BK (SEQ ID NO: 2) | 1.9 ± 0.2 | 3.2 ± 0.8 | 19.6 ± 0.9 |
| Met-Lys-BK (SEQ ID NO: 9) | 6.5 ± 1.5 | 16.1 ± 6.1 | 125 ± 10 |
| Des-Arg$^9$-BK (SEQ ID NO: 3) | 2,570 ± 756 | 4,260 ± 572 | 16,000 ± 1,270 |

Data are mean ± SEM from up to 13 independent experiments using cells derived from two different human donors' eyes (for h-TM and h-TM cells). h-NPE cells are immortalized human non-pigmented ciliary epithelial cells derived from the ciliary body. Partial agonist activity of Met-Lys-BK and Des-Arg$^9$-BK (E$_{max}$ = 70-77% relative to BK, 100%) was evident in h-NPE cells; all other agonists were full agonists in all cell-types. See FIG. 1 for concentration-response curves.

Figure 2A:
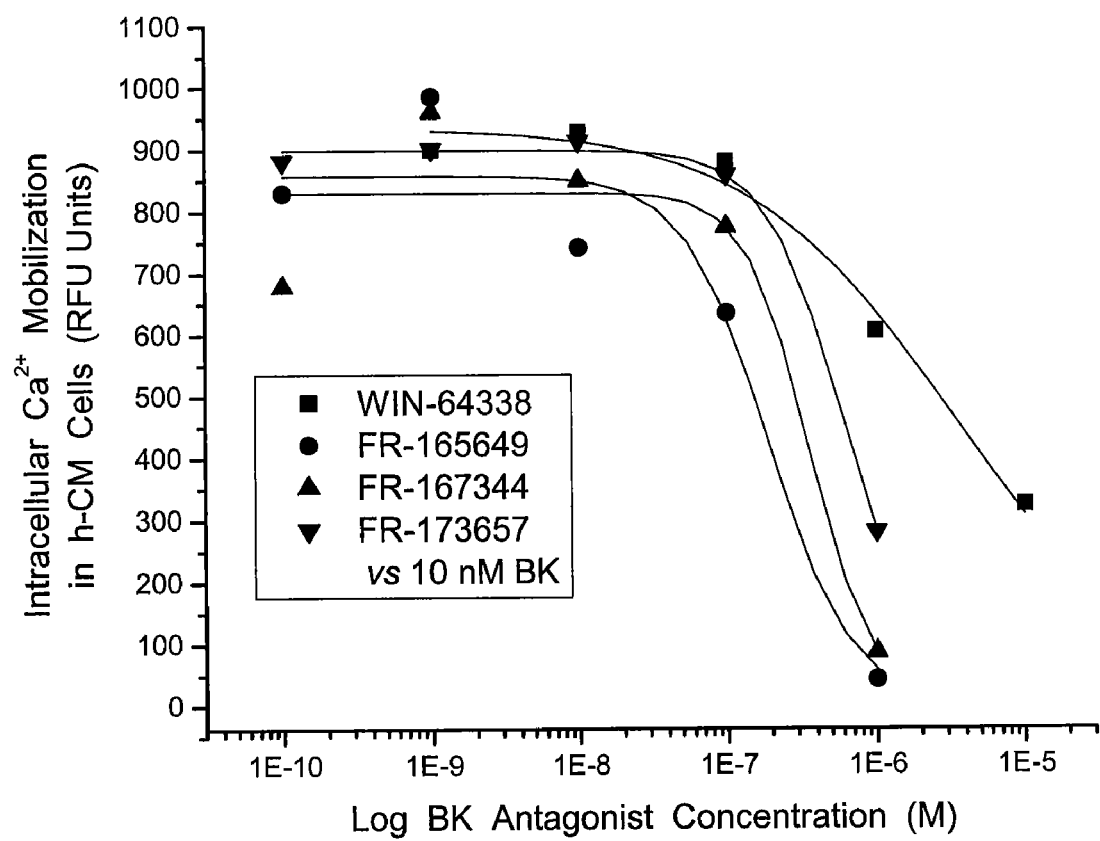
FIG. 2a and FIG. 2b illustrate the ability of various BK-antagonists to concentration-dependently antagonize the $[Ca^{2+}]_i$ mobilization induced by BK in human ciliary muscle and trabecular meshwork cells.
Figure 2B:
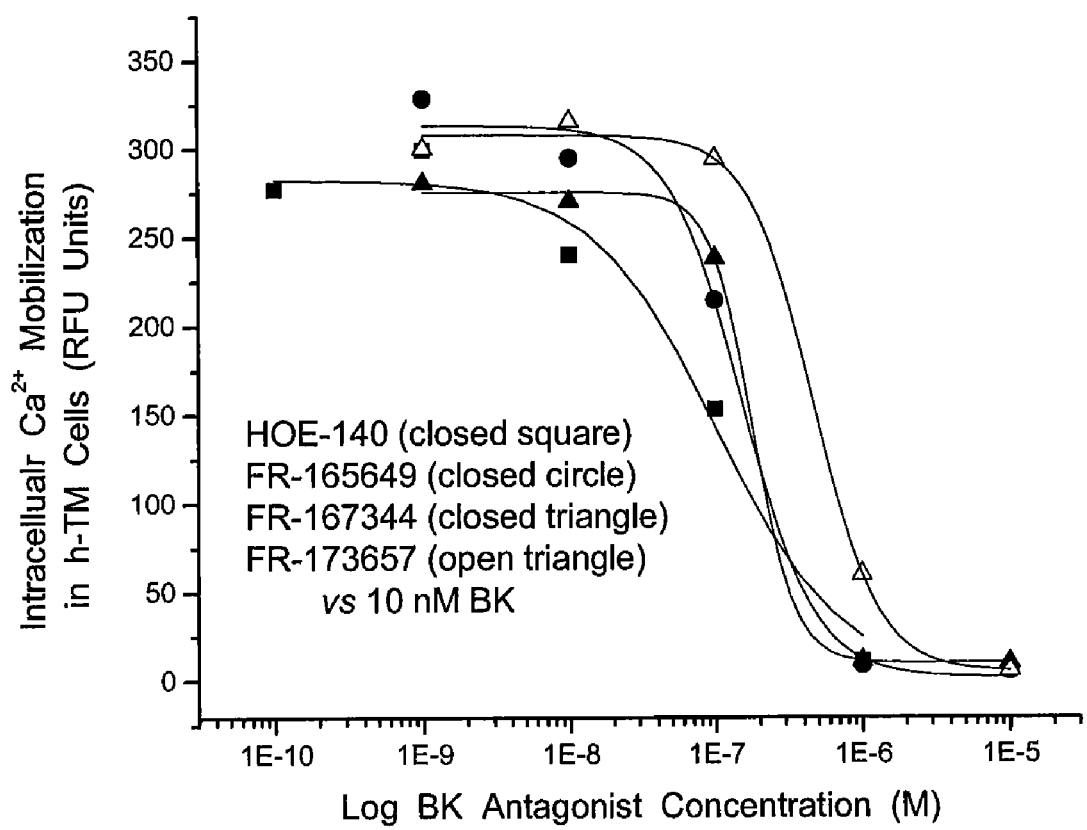

Importantly also, the agonist effects of BK could be blocked by the potent $B_2$-receptor antagonists HOE-140 and WIN-64338 and other non-peptide antagonists (Hall, *Pharmacol. Ther.* 56: 131-190, 1992; Leeb-Lundberg et al., *Pharmacol. Ther.* 57: 27-77, 2005; Abe et al., *J. Med. Chem.* 41: 4053-4061, 1998; Heitsch, *Curr. Med. Chem.* 9: 913-928, 2002) in h-TM, h-CM and h-NPE cells (Table 5; FIGS. 2a, 2b).

TABLE 5

Antagonism of BK-induced $[Ca^{2+}]_i$ Mobilization by Various BK $B_2$-Receptor Antagonists in Normal Primary Human Ocular TM, CM, and in Immortalized h-NPE Cells

| Antagonist | Antagonist Potency (K$_i$; nM) vs BK (10 nM) in $[Ca^{2+}]_i$ Mobilization Assay | | |
|---|---|---|---|
| | h-TM Cells | h-CM Cells | h-NPE Cells |
| HOE-140 | 4.9 ± 0.8 | 1.4 ± 0.1 | 7.9 ± 1.8 |
| WIN-64338 | 270 ± 28 | 174 ± 18 | 451 ± 44 |
| FR-165649 | 36, 387 | 11; 4 | 393; 337 |
| FR-167344 | 69; 19 | 13; 4 | 393; 223 |
| FR-173657 | 121, 193 | 35; 11 | 787; 788 |

Data are mean ± SEM where shown otherwise data from each individual experiment are shown. While HOE-140 is a peptidic antagonist, the other antagonists are non-peptides.

Figure 3:
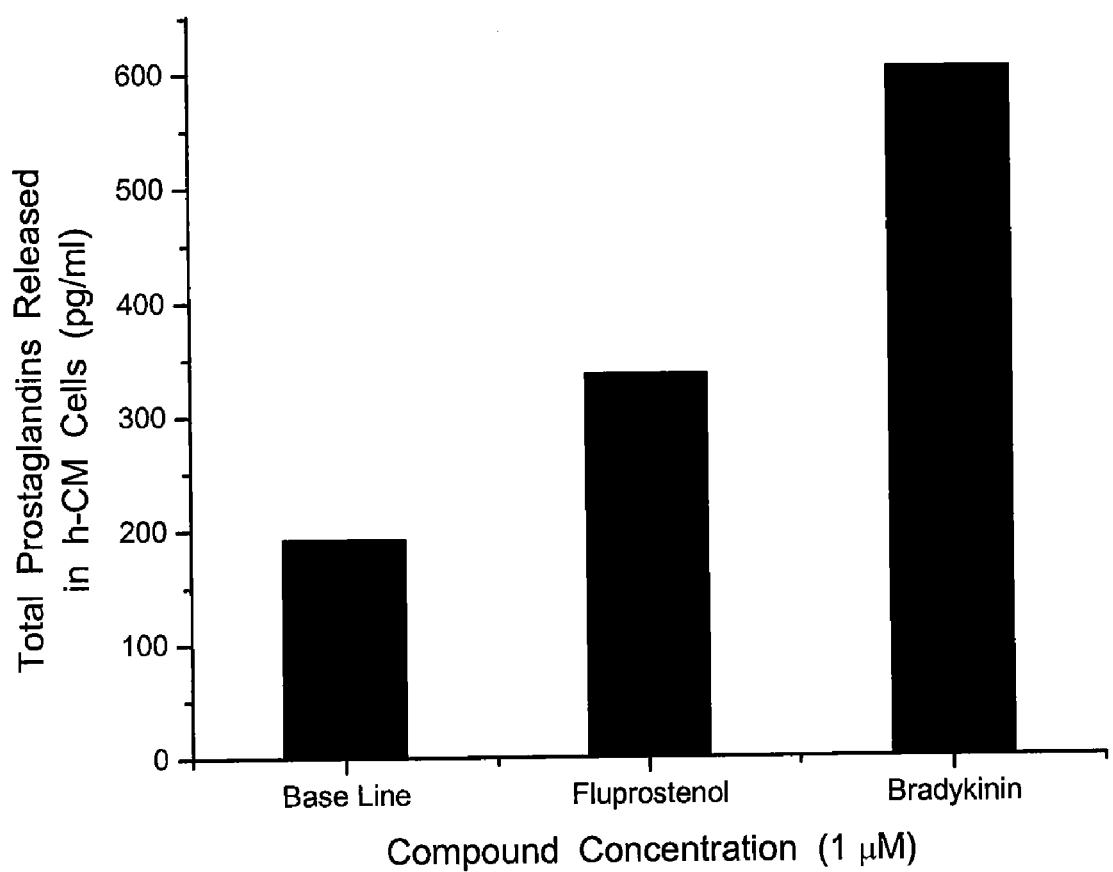
FIG. 3 illustrates the stimulation of production and release of endogenous prostaglandins by BK and fluprostenol from h-CM cells.

In addition, h-CM cells exposed to BK (1 µM) exhibited enhanced production of prostaglandins relative to baseline and relative to a synthetic IOP-lowering FP-class prostaglandin analog, fluprostenol, that mediates its effects partly by release of endogenous prostaglandins (FIG. 3).

Example 3

Figure 4:
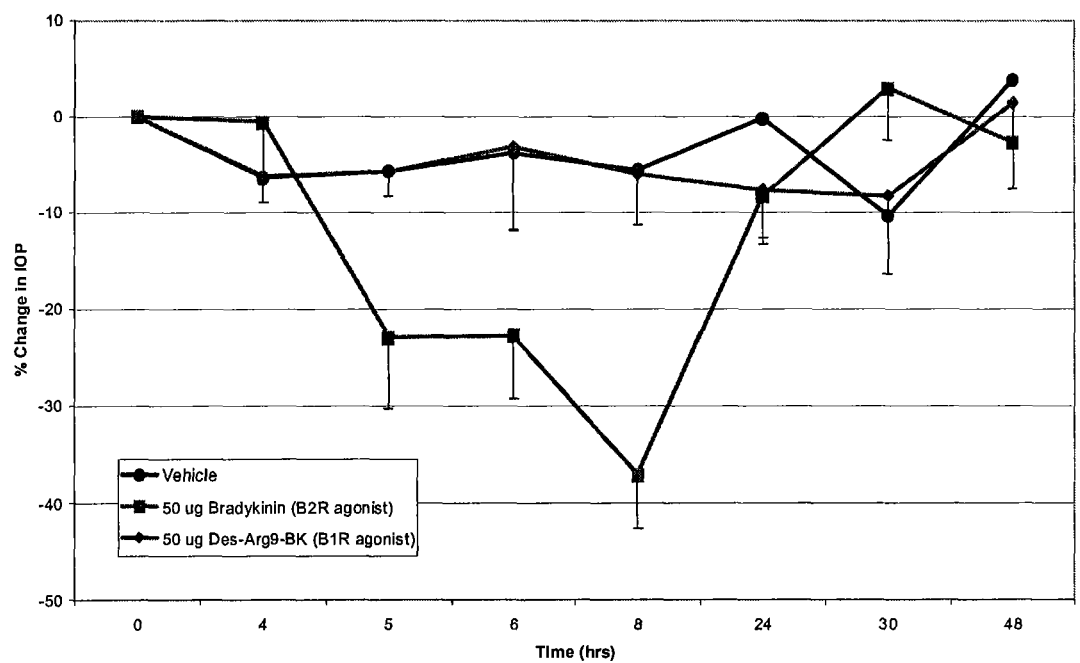
FIG. 4 is a graph showing that BK $B_2$ receptor ($B_2R$ agonist), but not Des-Arg$^9$-BK ($B_1R$ agonist), lowers IOP in Rabbit Eyes.

As shown in FIG. 4, intravitreally administered BK ($B_2$-receptor agonist; 50 µg), but not des-Arg9-BK ($B_1$-receptor agonist, 50 µg), profoundly lowered rabbit IOP relative to the effect of the vehicle alone. These results demonstrated that activation of the $B_2$ BK receptor caused ocular hypotension, and thus $B_2$ BK receptor agonists represented therapeutically useful agents to treat ocular hypertension and glaucoma. Conversely, non-peptidic BK antagonists dosed topical ocularly in the ocular hypertensive monkey eyes were ineffective at modulating IOP (see below Example 4).

Example 4

Bradykinin Antagonists do not Lower Monkey IOP

As shown in Table 6, non-peptide BK antagonists (LF-23-1591, WIN-64338 and FR-165649) topically administered (300 µg) to conscious cynomolgus monkeys failed to modulate IOP.

TABLE 6

Lack of Ocular Hypotensive Activity of Non-Peptidic $B_1$- and $B_2$-Receptor Antagonists in Conscious Ocular Hypertensive Cynomolgus Monkey Eyes

| Dose/time post-dose | % Change in IOP (mmHg) | | |
|---|---|---|---|
| | LF-23-1591 ($B_1$-Antagonist) | WIN-64338 ($B_2$-Antagonist) | FR-165649 ($B_2$-Antagonist) |
| Dose 1/1 hr | −4.8 ± 1.1 | 1.7 ± 1.6 | 1.0 ± 3.1 |
| Dose 1/3 hr | −6.6 ± 2.1 | −10.4 ± 2.8 | 0.7 ± 3.5 |
| Dose 1/6 hr | −6.8 ± 2.2 | 1.3 ± 1.3 | −6.2 ± 4.7 |
| Dose 1/24 hr | nd | nd | −4.0 ± 3.2 |

Data are mean ± SEM from 8-9 monkeys per study using two different groups of monkeys. The baseline IOPs were 37.4, 33.7, 37.4 and 37 mmHg, respectively, for these studies. The topical ocular dose was 300 µg. The vehicle had no effect on IOP. The IOP in the contralateral normotensive eyes was also unaffected.

nd = not determined.

It should be understood that the foregoing disclosure emphasizes certain specific embodiments of the invention and that all modifications or alternatives equivalent thereto are within the spirit and scope of the invention as set forth in the appended claims.

What is claimed is:

1. A method for controlling intraocular pressure in a patient comprising administering to the patient a composition comprising a pharmaceutically acceptable ophthalmic carrier and a therapeutically effective amount of a bradykinin $B_2$ receptor ($B_2R$) agonist, wherein the $B_2R$ agonist is not FR-190997 or Compound A, wherein the $B_2R$ agonist is administered topical ocular, sub-tenon, sub-conjunctivally, or intravitreally.

2. The method of claim 1, wherein the $B_2R$ agonist is a peptide or a pseudo-peptide bradykinin agonist or a prodrug thereof.

3. The method of claim 2, wherein the peptide bradykinin (BK) agonist is:

H-Arg-Pro-Pro-Gly-Phe-Ser-Pro-Phe-Arg-OH (SEQ ID NO: 1) (Bradykinin);

Lys-Arg-Pro-Pro-Gly-Phe-Ser-Pro-Phe-Arg (SEQ ID NO: 2);

H-D-Arg-Arg-Pro-Hyp-Gly-Thi-Ser-D-BT-Arg-OH (SEQ ID NO: 4);

H-Arg-Pro-Pro-Gly-Phe-Ser-D-BT-Arg-OH (SEQ ID NO: 5) (Compound 3);

H-Arg-Pro-Hyp-Gly-Thi-Ser-Pro-4-Me-Tyrψ(CH2NH)-Arg-OH (SEQ ID NO: 6) (RMP-7; Compound 4);

D-Arg-Arg-Pro-Hyp-Gly-Igl-Ser-Oic-Igl-Arg.TFA (SEQ ID NO: 7) (B9972; Compound 5);

H-D-Arg-Arg-Pro-Hyp-Gly-Thi-Ser-D-Tic-Oic-Arg-OH (SEQ ID NO: 8) (HOE-140; Icatibant; Compound 6);

Met-Lys-Arg-Pro-Pro-Gly-Phe-Ser-Pro-Phe-Arg (SEQ ID NO: 9);

Ile-Ser-Arg-Pro-Pro-Gly-Phe-Ser-Pro-Phe-Arg (SEQ ID NO: 10); or

Arg-Pro-Hyp-Gly-Phe-Ser-Pro-Phe-Arg (SEQ ID NO: 11).

4. The method of claim 1, wherein the patient has glaucoma.

5. The method of claim 1, wherein the patient has ocular hypertension.

6. The method of claim 1, further comprising administering to the patient a therapeutically effective amount of an aqueous humor production (inflow) inhibitor in combination with a suitable $B_2R$ agonist.

7. The method of claim 3, wherein the BK agonist is the R isomer of SEQ ID NO: 4.

8. The method of claim 3, wherein the BK agonist is the S isomer of SEQ ID NO: 4.

* * * * *

SEQUENCE LISTING

<160> NUMBER OF SEQ ID NOS: 25

<210> SEQ ID NO 1
<211> LENGTH: 9
<212> TYPE: PRT
<213> ORGANISM: Homo sapiens

<400> SEQUENCE: 1

Arg Pro Pro Gly Phe Ser Pro Phe Arg
1               5

<210> SEQ ID NO 2
<211> LENGTH: 10
<212> TYPE: PRT
<213> ORGANISM: Artificial
<220> FEATURE:
<223> OTHER INFORMATION: Synthetic peptide

<400> SEQUENCE: 2

Lys Arg Pro Pro Gly Phe Ser Pro Phe Arg
1               5                   10

<210> SEQ ID NO 3
<211> LENGTH: 8
<212> TYPE: PRT
<213> ORGANISM: Artificial
<220> FEATURE:
<223> OTHER INFORMATION: Synthetic peptide

<400> SEQUENCE: 3

Arg Pro Pro Gly Phe Ser Pro Phe
1               5

<210> SEQ ID NO 4
<211> LENGTH: 9
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X is trans-4-Hydroxy-L-proline
<220> FEATURE:
<221> NAME/KEY: MISC_FEATURE
<222> LOCATION: (6)..(6)
<223> OTHER INFORMATION: X is O-(2-thienyl)-alanine
<220> FEATURE:
<221> NAME/KEY: MISC_FEATURE
<222> LOCATION: (8)..(8)
<223> OTHER INFORMATION: X is a D-BT moiety

<400> SEQUENCE: 4

Arg Arg Pro Xaa Gly Xaa Ser Xaa Arg
1               5

<210> SEQ ID NO 5
<211> LENGTH: 8
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: X is a D-BT moiety

<400> SEQUENCE: 5

```
Arg Pro Pro Gly Phe Ser Xaa Arg
1               5
```

<210> SEQ ID NO 6
<211> LENGTH: 9
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X is trans-4-Hydroxy-L-proline
<220> FEATURE:
<221> NAME/KEY: MISC_FEATURE
<222> LOCATION: (5)..(5)
<223> OTHER INFORMATION: X is O-(2-thienyl)-alanine
<220> FEATURE:
<221> NAME/KEY: MISC_FEATURE
<222> LOCATION: (8)..(8)
<223> OTHER INFORMATION: X is 4-me-Tyrosine

<400> SEQUENCE: 6

```
Arg Pro Xaa Gly Xaa Ser Pro Xaa Arg
1               5
```

<210> SEQ ID NO 7
<211> LENGTH: 10
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X is trans-4-Hydroxy-L-proline
<220> FEATURE:
<221> NAME/KEY: MISC_FEATURE
<222> LOCATION: (6)..(6)
<223> OTHER INFORMATION: X is alpha-(2-Indanyl)glycine
<220> FEATURE:
<221> NAME/KEY: MISC_FEATURE
<222> LOCATION: (8)..(8)
<223> OTHER INFORMATION: X is Octahydroindole-2-carboxylic acid
<220> FEATURE:
<221> NAME/KEY: MISC_FEATURE
<222> LOCATION: (9)..(9)
<223> OTHER INFORMATION: X is alpha-(2-Indanyl)glycine
<220> FEATURE:
<221> NAME/KEY: MISC_FEATURE
<222> LOCATION: (10)..(10)
<223> OTHER INFORMATION: X is arginine.trifluoroacetic acid

<400> SEQUENCE: 7

```
Arg Arg Pro Xaa Gly Xaa Ser Xaa Xaa Xaa
1               5                   10
```

<210> SEQ ID NO 8
<211> LENGTH: 10
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X is trans-4-Hydroxy-L-proline
<220> FEATURE:
<221> NAME/KEY: MISC_FEATURE
<222> LOCATION: (6)..(6)
<223> OTHER INFORMATION: X is O-(2-thienyl)-alanine
<220> FEATURE:
<221> NAME/KEY: MISC_FEATURE

```
<222> LOCATION: (8)..(8)
<223> OTHER INFORMATION: X is L-1,2,3,4-Tetrahydroisoquinoline-3-
      carbonyl
<220> FEATURE:
<221> NAME/KEY: MISC_FEATURE
<222> LOCATION: (9)..(9)
<223> OTHER INFORMATION: X is Octahydroindole-2-carboxylic acid

<400> SEQUENCE: 8

Arg Arg Pro Xaa Gly Xaa Ser Xaa Xaa Arg
1               5                   10

<210> SEQ ID NO 9
<211> LENGTH: 11
<212> TYPE: PRT
<213> ORGANISM: Artificial
<220> FEATURE:
<223> OTHER INFORMATION: Synthetic peptide

<400> SEQUENCE: 9

Met Lys Arg Pro Pro Gly Phe Ser Pro Phe Arg
1               5                   10

<210> SEQ ID NO 10
<211> LENGTH: 11
<212> TYPE: PRT
<213> ORGANISM: Artificial
<220> FEATURE:
<223> OTHER INFORMATION: Synthetic peptide

<400> SEQUENCE: 10

Ile Ser Arg Pro Pro Gly Phe Ser Pro Phe Arg
1               5                   10

<210> SEQ ID NO 11
<211> LENGTH: 9
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X is trans-4-Hydroxy-L-proline

<400> SEQUENCE: 11

Arg Pro Xaa Gly Phe Ser Pro Phe Arg
1               5

<210> SEQ ID NO 12
<211> LENGTH: 9
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: X is p-chloro-Phe
<220> FEATURE:
<221> NAME/KEY: MISC_FEATURE
<222> LOCATION: (8)..(8)
<223> OTHER INFORMATION: X is p-chloro-Phe

<400> SEQUENCE: 12

Arg Pro Pro Gly Xaa Ser Pro Xaa Arg
1               5

<210> SEQ ID NO 13
```

```
<211> LENGTH: 9
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: X is 3,4-dehydro-Pro

<400> SEQUENCE: 13

Arg Xaa Xaa Gly Phe Ser Pro Phe Arg
1               5

<210> SEQ ID NO 14
<211> LENGTH: 8
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: X is 3,4-dehydro-Pro

<400> SEQUENCE: 14

Arg Xaa Xaa Gly Phe Ser Pro Phe
1               5

<210> SEQ ID NO 15
<211> LENGTH: 15
<212> TYPE: PRT
<213> ORGANISM: Artificial
<220> FEATURE:
<223> OTHER INFORMATION: Synthetic peptide

<400> SEQUENCE: 15

Lys Arg Pro Pro Gly Phe Ser Pro Phe Arg Ser Val Gln Val Ser
1               5                   10                  15

<210> SEQ ID NO 16
<211> LENGTH: 10
<212> TYPE: PRT
<213> ORGANISM: Artificial
<220> FEATURE:
<223> OTHER INFORMATION: Synthetic peptide

<400> SEQUENCE: 16

Lys Arg Pro Ala Gly Phe Ser Pro Phe Arg
1               5                   10

<210> SEQ ID NO 17
<211> LENGTH: 9
<212> TYPE: PRT
<213> ORGANISM: Artificial
<220> FEATURE:
<223> OTHER INFORMATION: Synthetic peptide

<400> SEQUENCE: 17

Lys Arg Pro Pro Gly Phe Ser Pro Phe
1               5

<210> SEQ ID NO 18
<211> LENGTH: 10
<212> TYPE: PRT
<213> ORGANISM: Artificial
<220> FEATURE:
<223> OTHER INFORMATION: Synthetic peptide
<220> FEATURE:
```

-continued

```
<221> NAME/KEY: MISC_FEATURE
<222> LOCATION: (4)..(4)
<223> OTHER INFORMATION: X is trans-4-Hydroxy-L-proline

<400> SEQUENCE: 18

Lys Arg Pro Xaa Gly Phe Ser Pro Phe Arg
1               5                   10

<210> SEQ ID NO 19
<211> LENGTH: 11
<212> TYPE: PRT
<213> ORGANISM: Artificial
<220> FEATURE:
<223> OTHER INFORMATION: Synthetic peptide

<400> SEQUENCE: 19

Lys Tyr Arg Pro Pro Gly Phe Ser Pro Phe Arg
1               5                   10

<210> SEQ ID NO 20
<211> LENGTH: 9
<212> TYPE: PRT
<213> ORGANISM: Artificial
<220> FEATURE:
<223> OTHER INFORMATION: Synthetic peptide

<400> SEQUENCE: 20

Arg Pro Pro Gly Phe Ser Phe Phe Arg
1               5

<210> SEQ ID NO 21
<211> LENGTH: 9
<212> TYPE: PRT
<213> ORGANISM: Artificial
<220> FEATURE:
<223> OTHER INFORMATION: Synthetic peptide

<400> SEQUENCE: 21

Arg Pro Pro Gly Phe Thr Pro Phe Arg
1               5

<210> SEQ ID NO 22
<211> LENGTH: 10
<212> TYPE: PRT
<213> ORGANISM: Artificial
<220> FEATURE:
<223> OTHER INFORMATION: Synthetic peptide

<400> SEQUENCE: 22

Tyr Arg Pro Pro Gly Phe Ser Pro Phe Arg
1               5                   10

<210> SEQ ID NO 23
<211> LENGTH: 9
<212> TYPE: PRT
<213> ORGANISM: Artificial
<220> FEATURE:
<223> OTHER INFORMATION: Synthetic peptide

<400> SEQUENCE: 23

Arg Pro Pro Gly Phe Ser Pro Tyr Arg
1               5

<210> SEQ ID NO 24
<211> LENGTH: 11
<212> TYPE: PRT
<213> ORGANISM: Artificial
```

-continued

```
<220> FEATURE:
<223> OTHER INFORMATION: Synthetic peptide

<400> SEQUENCE: 24

Met Lys Arg Ser Arg Gly Pro Ser Pro Arg Arg
1               5                   10

<210> SEQ ID NO 25
<211> LENGTH: 9
<212> TYPE: PRT
<213> ORGANISM: Artificial
<220> FEATURE:
<223> OTHER INFORMATION: Synthetic peptide

<400> SEQUENCE: 25

Arg Ser Arg Gly Pro Ser Pro Arg Arg
1               5
```